United States Patent
Lv et al.

(10) Patent No.: US 11,540,516 B2
(45) Date of Patent: *Jan. 3, 2023

(54) M-DIAMIDE COMPOUND AND PREPARATION METHOD THEREFOR AND USE THEREOF

(71) Applicant: CAC SHANGHAI INTERNATIONAL TRADING CO., LTD., Shanghai (CN)

(72) Inventors: Liang Lv, Shanghai (CN); Jiyong Liu, Shanghai (CN); Juncheng Xiang, Shanghai (CN); Wenjing Ma, Shanghai (CN); Liqi Zhou, Shanghai (CN); Shuang Hou, Shanghai (CN); Jueping Ni, Shanghai (CN); Zongcheng Li, Shanghai (CN)

(73) Assignee: CAC SHANGHAI INTERNATIONAL TRADING CO., LTD., Shanghai (CN)

(*) Notice: Subject to any disclaimer, the term of this patent is extended or adjusted under 35 U.S.C. 154(b) by 228 days.

This patent is subject to a terminal disclaimer.

(21) Appl. No.: 16/642,529

(22) PCT Filed: Mar. 12, 2019

(86) PCT No.: PCT/CN2019/077756
§ 371 (c)(1),
(2) Date: Feb. 27, 2020

(87) PCT Pub. No.: WO2020/001067
PCT Pub. Date: Jan. 2, 2020

(65) Prior Publication Data
US 2020/0178525 A1 Jun. 11, 2020

(30) Foreign Application Priority Data

Jun. 26, 2018 (CN) .......................... 201810669847.7
Dec. 18, 2018 (CN) .......................... 201811555432.3

(51) Int. Cl.
*A01N 37/18* (2006.01)
*C07C 237/42* (2006.01)
*C07C 255/50* (2006.01)

(52) U.S. Cl.
CPC ............ *A01N 37/18* (2013.01); *C07C 237/42* (2013.01); *C07C 255/50* (2013.01)

(58) Field of Classification Search
CPC ...... A01N 37/18; A01N 37/34; C07C 233/88; C07C 237/42; C07C 255/50; C07C 255/57; C07C 2601/02
See application file for complete search history.

(56) References Cited

U.S. PATENT DOCUMENTS

2009/0036547 A1 2/2009 Shah et al.
2015/0291510 A1 10/2015 Hueter et al.

FOREIGN PATENT DOCUMENTS

| | | | |
|---|---|---|---|
| CN | 101827521 | A | 9/2010 |
| CN | 102119143 | A | 7/2011 |
| CN | 108077303 | A | 5/2018 |
| CN | 108586279 | | 9/2018 |
| EA | 012040 | B1 | 6/2009 |
| JP | 2007099761 | | 4/2007 |
| JP | 2007099761 | A | 4/2007 |
| JP | 2013256522 | A | 12/2013 |
| RU | 2264099 | C2 | 11/2005 |
| RU | 2011140993 | A | 4/2013 |
| WO | 2006/137395 | A1 | 12/2006 |
| WO | 2010/018714 | A1 | 2/2010 |
| WO | 2017/104838 | A1 | 6/2017 |
| WO | 2018/011056 | A1 | 1/2018 |

OTHER PUBLICATIONS

JP2007099761A—English translation document (Year: 2007).*
Extended European Search Report issued in application No. 19827196.7, dated Sep. 7, 2021.
International Search Report issued in related PCT application No. PCT/CN2019/077756, dated May 29, 2019.

* cited by examiner

*Primary Examiner* — Umamaheswari Ramachandran
(74) *Attorney, Agent, or Firm* — Barnes & Thornburg LLP; Jeffrey R. Stone

(57) ABSTRACT

Provided are m-diamide compounds and a preparation method therefor and the use thereof. The m-diamide compounds have a structure represented by formula I. The m-diamide compounds of the present invention can have a high insecticidal activity at a low dose and take effect rapidly, can exert the insecticidal activity one day after application, can achieve a high insecticidal activity within three days, and have a good fast-acting property; moreover, due to the good effect at a low dose, the m-diamide compounds can reduce the damage to plants and human beings caused by excessive drug concentrations, enable less drug residue to be generated during application which is more conducive to environmental protection, and have broad application prospects.

15 Claims, No Drawings

M-DIAMIDE COMPOUND AND PREPARATION METHOD THEREFOR AND USE THEREOF

TECHNICAL FIELD

This invention belongs to the field of insecticide, relates to certain meta-carboxamido benzamide derivatives, their production process and pesticidal utility, in particular relates to 3-N-cyclopropyl methyl meta-carboxamido benzamide derivatives and their production process and pesticidal utility.

BACKGROUND

The damage caused by pests is still very significant in agriculture and horticulture. The emergence of insects showing resistance to various insecticides and environmental impact of existing pesticides are both serious problems, and new insecticides with better insecticidal activity at low concentration and environmentally-friendly are continually needed to be developed.

The preparation and insecticidal activities of meta-carboxamido benzamide derivatives have been disclosed. CN102119143A disclosed the structures and insecticidal activities of KC1 and KC2 (compounds 7-1574 and 7-1595 in the patent respectively). KC1 has been commercialized as an insecticide and its common name is broflanilide. These disclosed compounds have insecticidal activity, but their insecticidal activity is not good or slow at low concentration.

KC1

KC2

New insecticides with high insecticidal activity and quick efficacy at low concentration are still needed to meet the demands of agriculture and forestry industry.

SUMMARY

In view of the shortcomings of the prior art, the object of this invention is to provide certain meta-carboxamido benzamide derivatives, their production process and pesticidal utility, namely, 3-N-cyclopropyl methyl meta-carboxamido benzamide derivatives and their production process and pesticidal utility. The 3-N-cyclopropyl methyl meta-carboxamido benzamide derivatives in this invention have good insecticidal activity at low concentration and good quick-acting property. The 3-N-cyclopropyl methyl meta-carboxamido benzamide derivatives in this invention are used at low concentration, so they are more conducive to environmental protection.

In order to reach the above goals, this invention is specified by the following technical embodiments:

This invention provides meta-carboxamido benzamide derivatives (namely, 3-N-cyclopropyl methyl meta-carboxamido benzamide derivatives), which are defined by formula I:

Formula I

Wherein:

Z is selected from the group consisting of H, F, Cl, Br, I, CN, $NO_2$, $C_1$-$C_6$ alkyl, $C_1$-$C_6$ haloalkyl, $C_1$-$C_6$ alkoxyl, $C_1$-$C_6$ haloalkoxyl, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl;

$Y_1$ is selected from the group consisting of F, Cl, Br, I, CN, $NO_2$, $C_1$-$C_6$ alkyl, $C_1$-$C_6$ haloalkyl or $C_1$-$C_6$ haloalkoxyl;

$Y_2$ is $C_1$-$C_6$ haloalkyl;

$R_1$ is selected from the group consisting of H, F or $OCH_3$;

$R_2$ is selected from the group consisting of F or $CF_3$;

$R_3$ is selected from the group consisting of H, F, Cl, Br, I, $C_1$-$C_6$ alkyl, $C_1$-$C_6$ haloalkyl, $C_3$-$C_8$ cycloalkyl or $C_3$-$C_8$ halocycloalkyl;

$R_4$ is selected from the group consisting of H or halogen;

$W_1$ and $W_2$ are independently of each other O or S.

3-N-cyclopropyl methyl meta-carboxamido benzamide derivatives defined in formula I have excellent insecticidal activity and quick-acting properity. Their insecticidal activity could reach 80%, and even 90%-100% at low concentration. Their insecticidal activity can be exerted after one day of application and the excellent insecticidal activity can be achieved at the third day after application. The good insecticidal activity at low concentration of the meta-carboxamido benzamide derivatives in this invention can reduce the dose and the residue of pesticide, so they are more conducive to environmental protection.

Preference is given to compounds of formula I, in which

Z is selected from the group consisting of H, F, Cl, Br, I, CN, $NO_2$, $C_1$-$C_6$ alkyl, $C_1$-$C_6$ haloalkyl, $C_1$-$C_6$ alkoxyl, $C_1$-$C_6$ haloalkoxyl, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl;

$Y_1$ is selected from the group consisting of F, Cl, Br, I, CN, $NO_2$, $C_1$-$C_6$ alkyl, $C_1$-$C_6$ haloalkyl or $C_1$-$C_6$ haloalkoxyl;

$Y_2$ is $C_1$-$C_6$ haloalkyl;

$R_1$ is selected from the group consisting of F or $OCH_3$;

$R_2$ is F.

$R_3$ is selected from the group consisting of H, F, Cl, Br, I, $C_1$-$C_6$ alkyl, $C_1$-$C_6$ haloalkyl, $C_3$-$C_8$ cycloalkyl or $C_3$-$C_8$ halocycloalkyl;

$R_4$ is selected from the group consisting of H or halogen;

$W_1$ and $W_2$ are independently of each other O or S.

The more preferred compounds of formula I, in which is selected from the group consisting of H, F, Cl, Br, I, CN, $NO_2$, trifluoromethyl, pentafluoroethyl, heptafluoroisopropyl, difluoromethoxyl, trifluoromethoxyl, methylsulfinyl, trifluoromethyl sulfinyl, methylsulfonyl or trifluoromethyl sulfonyl;

$Y_1$ is selected from the group consisting of F, Cl, Br, I, CN, $NO_2$, methyl, i-propyl, trifluoromethyl, pentafluoroethyl, heptafluoroisopropyl or trifluoromethoxyl;

$Y_2$ is selected from the group consisting of trifluoromethyl, pentafluoroethyl or heptafluoroisopropyl;

$R_1$ is selected from the group consisting of F or methoxyl;

$R_2$ is F;

$R_3$ is selected from the group consisting of H, F, methyl, ethyl, n-propyl, i-propyl, n-butyl, i-butyl, t-butyl, ii-pentyl, l-methylbutyl, 2,2-dimethylpropyl, 2-methylbutyl, 1,3-dimethylbutyl, n-hexyl, monofluoromethyl, difluoromethyl, trifluoromethyl, monochloromethyl, dichloromethyl, trichloromethyl, pentafluoroethyl, heptafluoroisopropyl, cyclopropyl, cyclobutyl, cyclopentyl, perfluorocyclopropyl, perfluoro cyclobutyl or perfluorocyclopentyl;

$R_4$ is selected from the group consisting of H, F or Cl;

$W_1$ and $W_2$ are independently of each other O.

The more preferred compounds of formula I, in which the meta-carboxamido benzamide compound is any one selected from table 1.

TABLE 1

| Compound No. | Z | $W_1$ | $Y_1$ | $Y_2$ | $R_1$ | $R_2$ | $R_3$ | $R_4$ | Appearance (melting point: ° C.) |
|---|---|---|---|---|---|---|---|---|---|
| 1. | H | O | F | $CF_3$ | F | F | H | H | |
| 2. | H | O | Cl | $CF_3$ | F | F | H | H | |
| 3. | H | O | $NO_2$ | $CF_3$ | F | F | H | H | |
| 4 | H | O | Br | $CF_3$ | F | F | H | H | white solid(171.9-172.3) |
| 5. | H | O | I | $CF_3$ | F | F | H | H | |
| 6. | H | O | $CF_3$ | $CF_3$ | F | F | H | H | |
| 7. | H | O | Br | $CF_3$ | F | $CF_3$ | H | H | |
| 8. | H | O | Br | $CF_3$ | F | F | Me | H | yellow solid (78.4-80.0) |
| 9. | H | O | $CF_3$ | $CF_3$ | F | F | Me | H | |
| 10. | H | O | I | $CF_3$ | F | F | Me | H | |
| 11. | H | O | Br | $CF_3$ | OMe | F | Me | H | |
| 12. | H | O | Br | $CF_3$ | F | $CF_3$ | Me | H | |
| 13. | H | O | Br | $CF_3$ | F | F | $CH_2Cl$ | Cl | |
| 14. | H | S | Br | $CF_3$ | F | F | $CH_2Cl$ | Cl | |
| 15. | H | O | I | $CF_3$ | F | F | $CH_2Cl$ | Cl | |
| 16. | H | O | Br | $CF_3$ | OMe | F | $CH_2Cl$ | Cl | |
| 17. | H | O | Br | $CF_3$ | F | $CF_3$ | $CH_2Cl$ | Cl | |
| 18. | H | O | Br | $CF_3$ | F | F | $CF_3$ | H | |
| 19. | H | O | I | $CF_3$ | F | F | $CF_3$ | H | |
| 20. | H | O | Br | $CF_3$ | OMe | F | $CF_3$ | H | |
| 21. | H | O | Br | $CF_3$ | F | $CF_3$ | $CF_3$ | H | |
| 22. | H | O | Br | $CF_3$ | F | F | c-Pr | H | yellow solid (62.4-64.9) |
| 23. | CN | O | Br | $CF_3$ | F | F | H | H | yellow solid (129.5-131.3) |
| 24. | CN | O | Br | $CF_3$ | OMe | F | H | H | yellow solid (152.3-153.5) |
| 25. | CN | O | Br | $CF_3$ | F | $CF_3$ | H | H | |
| 26. | CN | O | Br | $CF_3$ | F | F | Me | H | yellow solid (102.0-103.5) |
| 27. | CN | O | Br | $CF_3$ | F | $CF_3$ | Me | H | |
| 28. | CN | O | Br | $CF_3$ | F | F | $CF_3$ | H | |
| 29. | CN | O | Br | $CF_3$ | OMe | F | $CF_3$ | H | |
| 30. | CN | O | Br | $CF_3$ | F | $CF_3$ | $CF_3$ | H | |
| 31. | CN | O | Br | $CF_3$ | F | F | $CH_2Cl$ | Cl | |
| 32. | CN | O | Br | $CF_3$ | F | F | c-Pr | H | pale yellow solid (73.5-76.1) |
| 33. | CN | O | Br | $CF_3$ | F | $CF_3$ | c-Pr | H | |
| 34. | CN | S | Br | $CF_3$ | F | F | H | H | |
| 35. | CN | S | Br | $CF_3$ | OMe | F | H | H | |
| 36. | CN | S | Br | $CF_3$ | F | F | $CF_3$ | H | |
| 37. | $CF_3$ | O | Br | $CF_3$ | F | F | H | H | yellow solid (132.5-134.3) |
| 38. | $CF_3$ | O | Br | $CF_3$ | OMe | F | H | H | pale yellow solid (140.6-142.5) |
| 39. | $CF_3$ | O | Br | $CF_3$ | F | F | Me | H | yellow solid (90.7-92.6) |
| 40. | $CF_3$ | O | Br | $CF_3$ | F | F | c-Pr | H | |
| 41. | Cl | O | Br | $CF_3$ | F | F | H | H | yellow solid (141.2-142.0) |
| 42. | Cl | O | Br | $CF_3$ | F | $CF_3$ | H | H | |
| 43. | Cl | O | Br | $CF_3$ | OMe | F | H | H | pale yellow solid (139.3-140.2) |
| 44. | Cl | O | Br | $CF_3$ | F | F | Me | H | yellow solid (95.3-97.2) |
| 45. | Cl | O | Br | $CF_3$ | F | F | c-Pr | H | |

TABLE 1-continued

| Compound No. | Z | W₁ | Y₁ | Y₂ | R₁ | R₂ | R₃ | R₄ | Appearance (melting point: °C.) |
|---|---|---|---|---|---|---|---|---|---|
| 46. | Br | O | Br | $CF_3$ | F | F | H | H | brown solid(135.1-137.0) |
| 47. | Br | O | I | $CF_3$ | F | F | H | H | yellow oil |
| 48. | Br | O | Br | $CF_3$ | F | $CF_3$ | H | H | |
| 49. | Br | O | Br | $CF_3$ | OMe | F | H | H | white solid(144.5-146.5) |
| 50. | Br | O | Br | $CF_3$ | F | F | Me | H | white solid (99.9-101.1) |
| 51. | Br | O | Br | $CF_3$ | F | F | c-Pr | H | |
| 52. | I | O | Br | $CF_3$ | F | F | H | H | yellow solid (142.2-143.5) |
| 53. | I | O | I | $CF_3$ | F | F | H | H | yellow solid (96.1-97.5) |
| 54. | I | O | Br | $CF_3$ | F | $CF_3$ | H | H | |
| 55. | I | O | Br | $CF_3$ | OMe | F | H | H | |
| 56. | Me | O | Br | $CF_3$ | F | F | H | H | |
| 57. | $MeS(O)_2$ | O | Br | $CF_3$ | F | F | H | H | dark yellow solid (171.7-173.1) |
| 58. | $CF_3S(O)_2$ | O | Br | $CF_3$ | F | F | H | H | |
| 59. | $NO_2$ | O | Br | $CF_3$ | F | F | H | H | |
| 60. | $OCF_3$ | O | Br | $CF_3$ | F | F | H | H | yellow oil |
| 61. | H | S | Br | $CF_3$ | F | F | H | H | |
| 62. | F | O | Br | $CF_3$ | F | F | H | H | yellow solid (141.6-143.7) |
| 63. | F | O | Br | $CF_3$ | F | F | Me | H | white solid(68.7-70.8) |
| 64. | H | O | Br | $CF_3$ | F | F | Me | Cl | |
| 65. | H | O | Br | $CF_3$ | F | F | $CH_2F$ | Cl | |
| 66. | Cl | O | Br | $CF_3$ | F | F | Me | Cl | |
| 67. | Cl | O | Br | $CF_3$ | F | F | $CH_2Cl$ | Cl | |
| 68. | Cl | O | Br | $CF_3$ | F | F | $CH_2F$ | Cl | |
| 69. | Br | O | Br | $CF_3$ | F | F | Me | Cl | |
| 70. | Br | O | Br | $CF_3$ | F | F | $CH_2Cl$ | Cl | |
| 71. | Br | O | Br | $CF_3$ | F | F | $CH_2F$ | Cl | |
| 72. | $CF_3$ | O | Br | $CF_3$ | F | F | Me | Cl | |
| 73. | $CF_3$ | O | Br | $CF_3$ | F | F | $CH_2Cl$ | Cl | |
| 74. | $CF_3$ | O | Br | $CF_3$ | F | F | $CH_2F$ | Cl | |
| 75. | CN | O | Br | $CF_3$ | F | F | Me | Cl | yellow solid (83.9-87.3) |
| 76. | CN | O | Br | $CF_3$ | F | F | $CH_2F$ | Cl | |
| 77. | $MeS(O)_2$ | O | Br | $CF_3$ | F | F | H | Me | pale yellow solid (76.0-78.8) |

Comments on compounds in Table 1: $W_2$ is O, "H" represents hydrogen, "F" represents fluorine, "Cl" represents chlorine, "Br" represents bromine, "I" represents iodine, "CN" represents cyano, "$NO_2$" represents nitro, "OMe" represents methoxyl, "$CH_2Cl$" represents monochloromethyl, "$CH_2F$" represents monofluoromethyl, "$CF_3$," represents trifluoromethyl, "$OCF_3$" represents trifluoromethoxyl, "$OCF_2H$" represents difluoromethoxyl, "c-Pr" represents cyclopropyl, "$MeS(O)_2$" represents methylsulfonyl, and "$CF_3S(O)_2$" represents trifluoromethyl sulfonyl.

The further more preferred compounds of formula I, in which

Z is selected from the group consisting of H, F, Cl, Br, I, CN, $NO_2$, trifluoromethyl, trifluoromethoxyl, methylsulfonyl or trifluoromethyl sulfonyl;

$Y_1$ is selected from the group consisting of Br or I;

$Y_2$ is trifluoromethyl group;

$R_1$ is selected from the group consisting of F or methoxyl;

$R_2$ is F;

$R_3$ is selected from the group consisting of H, methyl or cyclopropyl;

$R_4$ is selected from the group consisting of H or Cl.

The particular preferred compounds of formula I, in which the meta-carboxamido benzamide compounds is selected from any one compound below or a combination of at least two compounds below:

N-(2-bromo-4-(perfluoropropan-2-yl)-6-(trifluoromethyl)phenyl)-3-(N-(cyclopropylmethyl)benzamido)-2-fluorobenzamide;

N-(2-bromo-4-(perfluoropropan-2-yl)-6-(trifluoromethyl)phenyl)-3-(N-(1-cyclopropylethyl)benzamido)-2-fluorobenzamide;

N-(2-bromo-4-(perfluoropropan-2-yl)-6-(trifluoromethyl)phenyl)-3-(N-(dicyclopropylmethyl)benzamido)-2-fluorobenzamide;

N-(2-bromo-4-(perfluoropropan-2-yl)-6-(trifluoromethyl)phenyl)-3-(4-cyano-N-(cyclopropylmethyl)benzamido)-2-fluorobenzamide;

N-(2-bromo-4-(1,1,1,3,3,3-hexafluoro-2-methoxypropan-2-yl)-6-(trifluoromethyl)phenyl)-3-(4-cyano-N-(cyclopropylmethyl)benzamido)-2-fluorobenzamide;

N-(2-bromo-4-(perfluoropropan-2-yl)-6-(trifluoromethyl)phenyl)-3-(4-cyano-N-(1-cyclopropylethyl)benzamido)-2-fluorobenzamide;

N-(2-bromo-4-(perfluoropropan-2-yl)-6-(trifluoromethyl)phenyl)-3-(4-cyano-N-(dicyclopropylmethyl)benzamido)-2-fluorobenzamide;

N-(2-bromo-4-(perfluoropropan-2-yl)-6-(trifluoromethyl)phenyl)-3-(N-(cyclopropylmethyl)-4-(trifluoromethyl)benzamido)-2-fluorobenzamide;

N-(2-bromo-4-(1,1,1,3,3,3-hexafluoro-2-methoxypropan-2-yl)-6-(trifluoromethyl)phenyl)-3-(N-(cyclopropylmethyl)-4-(trifluoromethyl)benzamido)-2-fluorobenzamide;

N-(2-bromo-4-(perfluoropropan-2-yl)-6-(trifluoromethyl)phenyl)-3-(N-(1-cyclopropylethyl)-4-(trifluoromethyl)benzamido)-2-fluorobenzamide;

N-(2-bromo-4-(perfluoropropan-2-yl)-6-(trifluoromethyl)
phenyl)-3-(4-chloro-N-(cyclopropylmethyl)benzamido)-
2-fluorobenzamide;
N-(2-bromo-4-(1,1,1,3,3,3-hexafluoro-2-methoxypropan-2-
yl)-6-(trifluoromethyl)phenyl)-3-(4-chloro-N-(cyclopro-
pylmethyl)benzamido)-2-fluorobenzamide;
N-(2-bromo-4-(perfluoropropan-2-yl)-6-(trifluoromethyl)
phenyl)-3-(4-chloro-N-(1-cyclopropylethyl)benzamido)-
2-fluorobenzamide;
N-(2-bromo-4-(perfluoropropan-2-yl)-6-(trifluoromethyl)
phenyl)-3-(4-bromo-N-(cyclopropylmethyl)benzamido)-
2-fluorobenzamide;
N-(2-iodo-4-(perfluoropropan-2-yl)-6-(trifluoromethyl)phe-
nyl)-3-(4-bromo-N-(cyclopropylmethyl)benzamido)-2-
fluorobenzamide;
N-(2-bromo-4-(1,1,1,3,3,3-hexafluoro-2-methoxypropan-2-
yl)-6-(trifluoromethyl)phenyl)-3-(4-bromo-N-(cyclopro-
pylmethyl)benzamido)-2-fluorobenzamide;
N-(2-bromo-4-(perfluoropropan-2-yl)-6-(trifluoromethyl)
phenyl)-3-(4-bromo-N-(1-cyclopropylethyl)benzamido)-
2-fluorobenzamide;
N-(2-bromo-4-(perfluoropropan-2-yl)-6-(trifluoromethyl)
phenyl)-3-(N-(cyclopropylmethyl)-4-iodobenzamido)-2-
fluorobenzamide;
N-(2-iodo-4-(perfluoropropan-2-yl)-6-(trifluoromethyl)phe-
nyl)-3-(N-(cyclopropylmethyl)-4-iodobenzamido)-2-
fluorobenzamide;
N-(2-bromo-4-(perfluoropropan-2-yl)-6-(trifluoromethyl)
phenyl)-3-(N-(cyclopropylmethyl)-4-(methylsulfonyl)
benzamido)-2-fluorobenzamide;
N-(2-bromo-4-(perfluoropropan-2-yl)-6-(trifluoromethyl)
phenyl)-3-(N-(cyclopropylmethyl)-4-(trifluoromethoxy)
benzamido)-2-fluorobenzamide;
N-(2-bromo-4-(perfluoropropan-2-yl)-6-(trifluoromethyl)
phenyl)-3-(N-(cyclopropylmethyl)-4-fluorobenzamido)-
2-fluorobenzamide;
N-(2-bromo-4-(perfluoropropan-2-yl)-6-(trifluoromethyl)
phenyl)-3-(N-(1-cyclopropylethyl)-4-fluorobenzamido)-
2-fluorobenzamide;
N-(2-bromo-4-(perfluoropropan-2-yl)-6-(trifluoromethyl)
phenyl)-3-(N-(1-(1-chlorocyclopropyl)ethyl)-4-cyano-
benzamido)-2-fluorobenzamide;
N-(2-bromo-4-(perfluoropropan-2-yl)-6-(trifluoromethyl)
phenyl)-3-(N-(1-cyclopropylethyl)-4-(methyl sulfonyl)
benzamido)-2-fluorobenzamide.

The alkyl in present invention represents a straight-chain or branched alkyl group, for example methyl, ethyl, n-propyl, i-propyl, n-butyl, i-butyl, s-butyl, i-butyl, n-pentyl, i-pentyl, n-hexyl, and the like. Haloalkyl represents alkyl substituted by one or more halogen atoms which may be the same as or different from each other. Alkoxyl represents the alkyl substituted by oxygen atom, for example, methoxyl, ethoxyl, n-propoxyl, i-propoxyl, t-butxoyl, and the like. Haloalkoxyl represents alkoxyl substituted by one or more halogen atoms which may be the same as or different from each other. Halogen means F, Cl, Br or I.

As used herein, the term "$C_1$-$C_6$ alkyl" represents straight-chain or branched alkyl group having 1 to 6 carbon atoms, including but not limiting to methyl, ethyl, n-propyl, i-propyl, n-butyl, i-butyl, s-butyl, t-butyl, n-pentyl, i-pentyl, n-hexyl and the like. The term "$C_1$-$C_6$ alkoxyl" represents straight-chain or branched alkoxyl group having 1 to 6 carbon atoms, including but not limiting to methoxyl, ethoxyl, n-propoxyl, t-butxoyl, and the like. "$C_1$-$C_6$ haloalkyl" represents a straight-chain or branched alkyl group having 1 to 6 carbon atoms, that is substituted with one or more halogen atoms which may be the same as or different from each other, including but not limiting to trifluoromethyl, pentafluoroethyl, heptafluoropropyl, heptafluoroisopropyl and the like. The term "$C_3$-$C_8$ cycloalkyl" represents cycloalkyl group having 3 to 8 carbon atoms, including but not limiting to cyclopropyl, cyclobutyl, cyclopentyl, cyclohexyl, cycloheptanyl, cyclooctyl and the like. "$C_3$-$C_8$ halocycloalkyl" represents cycloalkyl group having 3 to 8 carbon atoms, which is substituted with one or more halogen atoms which may be the same as or different from each other, including but not limiting to 1-chlorocyclopropyl, 1-fluorocyclopropyl, perfluorocyclopropyl, 1-chlorocyclopentyl, 1-chlorocyclobutyl and the like.

$C_1$-$C_6$, $C_3$-$C_8$ and the like in front of specific group mean the number of carbon atoms contained in the group, for example, $C_1$-$C_6$ represents the group contains 1, 2, 3, 4, 5 or 6 carbon atoms, $C_3$-$C_8$ represents the group contains 3, 4, 5, 6, 7 or 8 carbon atoms, $C_2$-$C_4$ represents the group contains 2, 3 or 4 carbon atoms, and the like.

Furthermore, "i-" means iso, "s-" means secondary and "t-" means tertiary, "Me" represents methyl, "Et" represents ethyl, "i-Pr" represents iso-propyl, "c-Pr" represents cyclopropyl, "c-Bu" represents cyclobutyl, "c-Pent" represents cyclopentyl, "c-Hex" represents cyclohexyl, "$CF_3$" represents trifluoromethyl, "$OCF_3$" represents trifluoromethoxyl, "$OCF_2H$" represents difluoromethoxyl, "H" represents hydrogen, "F" represents fluorine, "Cl" represents chlorine, "Br" represents bromine, "I" represents iodine, "O" represents oxygen, "S" represents sulfur atom, "Ac" represents acetyl, "OMe" represents methoxyl, "OEt" represents ethoxyl, "O-(i-Pr)" represents i-propoxyl, "MeS(O)$_2$" represents methylsulfonyl, "$CF_3S(O)_2$" represents trifluoromethyl sulfonyl, "CN" represents cyano, "$NO_2$" represents nitro.

Compounds of formula I can be prepared by following methods. Each group of them is defined above, unless otherwise specified.

Preparation Method 1

The structures of the compounds represented by general formula I according to this invention are as follows, which can be prepared by the following methods.

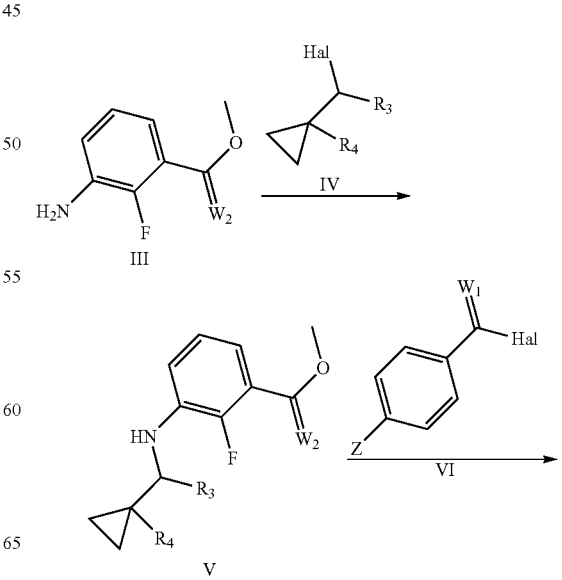

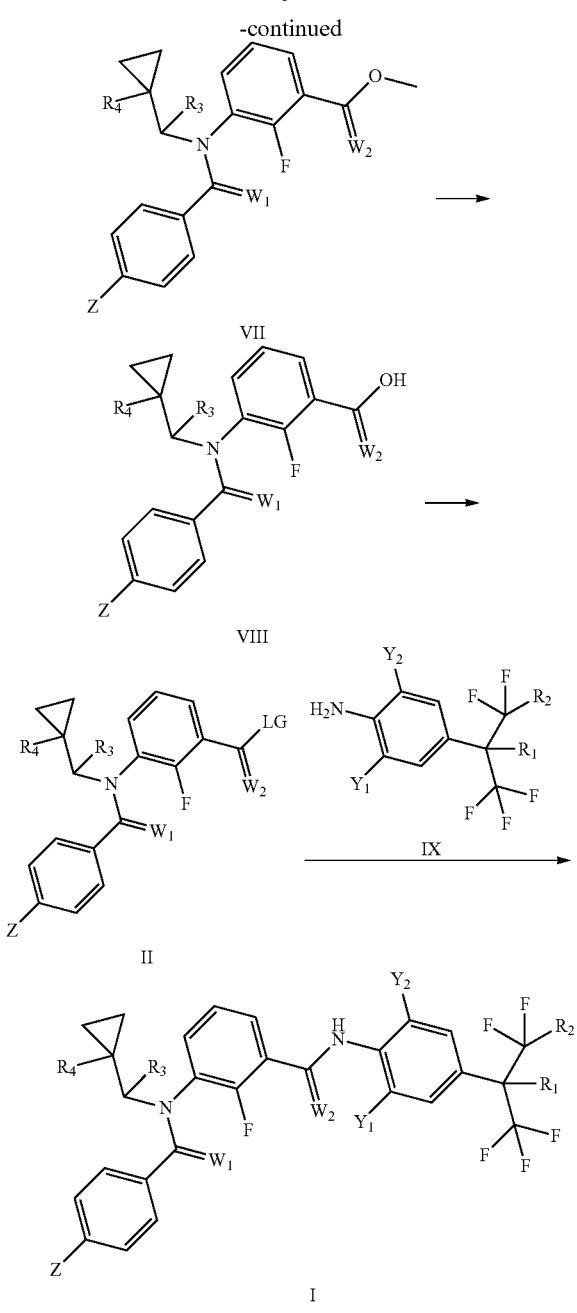

Wherein, the LG is selected from the group consisting of F, Cl, Br, $C_1$-$C_{12}$ alkoxyl, $C_1$-$C_{12}$ alkoxyl acyloxyl or $C_1$-$C_{12}$ alkyl acyloxyl; Hal is selected from the group consisting of F, Cl, Br or I; $R_1$, $R_2$, $R_3$, $R_4$, Z, $Y_1$, $Y_2$, $W_1$, $W_2$ are defined identically as above, and will not be repeated here.

1-(i): Formula III+Formula IV→Formula V

Preferably, the compound represented by Formula III can be suitably selected in the range of 0.5 to 2 mole equivalents based on the compound represented by Formula IV, such as 0.5:1, 0.8:1, 1:1, 1.2:1, 1.4:1, 1.5:1, 1.8:1 or 2:1.

In the process of the reaction 1-(i), a base can be used, including organic bases and/or inorganic bases.

Preferably, examples of the organic bases include any one of triethylamine, N, N-diisopropylethylamine, N,N-dimethylaniline, pyridine, sodium carbonate, potassium carbonate, sodium methoxide, sodium ethoxide, sodium tert-butoxide, potassium tert-butoxide or a combination of at least two thereof.

Preferably, examples of the inorganic bases include any one of sodium hydroxide, potassium hydroxide or sodium hydride or a combination of at least two thereof.

Preferably, solvents of the reaction 1-(i) include any one of dichloromethane, chloroform, toluene, ethyl acetate, acetone, acetonitrile, tetrahydrofuran, dioxane, N, N-dimethylformamide, dimethyl sulfoxide or hexamethylphosphatidyl triamide or a combination of at least two thereof.

Preferably, the reaction temperature of the reaction 1-(i) can be appropriately selected within the range from room temperature to the boiling point of the solvent used, such as 25° C., 30° C., 35° C., 40° C., 45° C., 50° C., 60° C., 70° C., 75° C., 80° C., 85° C., 90° C. or the boiling point, i.e., the reflux temperature of the solvent used.

Preferably, the reaction time of 1-(i) can be appropriately selected within the range from half an hour to 48 hours, such as 0.5 hour, 1 hour, 3 hours, 5 hours, 8 hours, 10 hours, 12 hours, 15 hours, 18 hours, 20 hours, 23 hours, 25 hours, 28 hours, 30 hours, 33 hours, 35 hours, 38 hours, 40 hours, 44 hours or 48 hours.

1-(ii): Formula V+Formula VI→Formula VII

By reacting a compound represented by the general Formula V with a compound represented by the general Formula VI, a compound represented by the general Formula VII can be prepared.

Preferably, the compound represented by Formula V can be suitably selected in the range of 0.5 to 2 mole equivalents based on the compound represented by Formula VI, such as 0.5:1, 0.8:1, 1:1, 1.2:1, 1.4:1, 1.6:1, 1.8:1 or 2:1.

In the process of the reaction 1-(ii), a base can be used, including organic bases and or inorganic bases.

Preferably, examples of the organic bases include any one of triethylamine, N, N-diisopropylethylamine, N,N-dimethylaniline, pyridine, sodium carbonate, potassium carbonate, sodium methoxide, sodium ethoxide, sodium tert-butoxide, potassium tert-butoxide or a combination of at least two thereof.

Preferably, examples of the inorganic bases include any one of sodium hydroxide, potassium hydroxide or sodium hydride or a combination of at least two thereof.

Preferably, solvents of the reaction 1-(ii) include any one of dichloromethane, chloroform, toluene, ethyl acetate, acetonitrile, tetrahydrofuran, dioxane, N, N-dimethylformamide, dimethyl sulfoxide or hexamethylphosphatidyl triamide or a combination of at least two thereof.

Preferably, the reaction temperature of t 1-(ii) can be appropriately selected within the range from −10° C. to the boiling point of the solvent used, such as −10° C., −5° C. 0° C., 5° C., 10° C., 15° C., 20° C., 25° C., 30° C., 35° C., 40° C., 45° C., 50° C., 60° C., 70° C., 75° C., 80° C., 85° C., 90° C. or boiling point, i.e., the reflux temperature of the solvent used.

Preferably, the reaction time of 1-(ii) can be appropriately selected within the range from half an hour to 48 hours, such as 0.5 hour, 1 hour, 3 hours, 5 hours, 8 hours, 10 hours, 12 hours, 15 hours, 18 hours, 20 hours, 23 hours, 25 hours, 28 hours, 30 hours, 33 hours, 35 hours, 38 hours, 40 hours, 44 hours or 48 hours.

1-(iii): Formula VII→Formula VIII

By hydrolysing a compound represented by the general Formula VII, a compound represented by the general Formula VIII can be obtained.

The hydrolysis reaction of 1-(iii) is conducted in any one of water, methanol, ethanol, tetrahydrofuran, dioxane or the mixture of at least two thereof.

Preferably, in the process of the reaction 1-(iii), a base can also be used, preferably including lithium hydroxide, sodium hydroxide or potassium hydroxide.

Preferably, the base can be suitably selected in the range of 1 to 5 mole equivalents based on the compound represented by Formula VII, such as 1.0:1, 1.3:1, 1.5:1, 1.8:1, 2.0:1, 2.5:1, 3.0:1, 3.5:1, 4.0:1, 4.5:1, or 5.0:1.

1-(iv): Formula VIII→Formula II

A compound represented by the general formula II having a leaving group can be prepared by a well-known method reacting a compound represented by the general formula VIII with thionyl chloride, oxalyl chloride, carbonyl chloride, phosphoryl chloride, phosphorus pentachloride, phosphorus trichloride, thionyl bromide, triphosgene, isopropyl trichloroformate or the like.

1-(v): Formula II+Formula IX→Formula I

By reacting a compound represented by the general Formula II with a compound represented by the general Formula IX, a compound represented by the general Formula I can be prepared.

Preferably, the compound represented by Formula II can be suitably selected in the range of 0.5 to 2 mole equivalents based on the compound represented by Formula IX, such as 0.5:1, 0.8:1, 1:1, 1.2:1, 1.4:1, 1.6:1, 1.8:1 or 2:1.

In the process of the reaction 1-(v), a base can be used, including organic bases and/or inorganic bases.

Preferably, examples of the organic bases include any one of trimethylamine, triethylamine, N,N-diisopropylethylamine, tributylamine, pyridine, piperidine, 3-methylpyridine, 2,6-dimethylpyridine, N-methylmorpholine, 3-methylimidazole, 4-N, N-dimethylaminopyridine, alkali alcoholate, lithium amino or a combination of at least two thereof.

Preferably, the alkali alcoholate is sodium methoxide and/or sodium ethoxide. And the lithium amino is lithium diisopropylamide.

Preferably, the inorganic bases include any one of alkali metal hydroxides, carbonates, phosphates or a combination of at least two thereof.

Preferably, the alkali metal hydroxides contain any one of lithium hydroxide, sodium hydroxide, potassium hydroxide or a combination of at least two thereof. Preferably, the alkali metal carbonates include any one of sodium bicarbonate, sodium carbonate, potassium carbonate or a combination of at least two thereof. Preferably, the alkali metal phosphates include dipotassium hydrogen phosphate and/or trisodium phosphate.

Preferably, the solvents of 1-(v) may be any of those which do not inhibit the present reaction significantly. The solvent can include any one of halogenated hydrocarbons, aromatic hydrocarbons, chained or cyclic ethers, esters, ketones, nitriles, polar aprotic inert solvents or a combination of at least two thereof.

Preferably, the halogenated hydrocarbons include any one of methylene dichloride, chloroform or carbon tetrachloride or a combination of at least two thereof. Preferably, the aromatic hydrocarbons include any one of benzene, toluene, xylene, chlorobenzene or dichlorobenzene or a combination of at least two thereof. Preferably, the chained or cyclic ethers include any one of ether, tetrahydrofuran, dioxane or 1,2-dimethoxyethane or a combination of at least two thereof. Preferably, the esters include ethyl acetate and/or butyl acetate. Preferably, the ketones include any one of acetone, methyl isobutyl ketone, cyclohexanone or a combination of at least two thereof. Preferably, the nitriles include acetonitrile and/or acrylonitrile.

Preferably, the polar aprotic inert solvents include any one of 1, 3-dimethyl-2-imidazolinone, sulfolane, dimethyl sulfoxide, N, N-dimethylformamide, N-methylpyrrolidone, N,N-dimethylacetamide or hexamethylphosphamide or a combination of at least two thereof.

Preferably, the reaction temperature of the reaction 1-(v) can be appropriately selected within the range from −70° C. to the boiling point of the solvent used, such as −70° C., −50° C., −30° C., −10° C., −5° C., 0° C., 5° C., 15° C., 25° C., 30° C., 35° C., 40° C., 45° C., 50° C., 60° C., 70° C., 75° C., 80° C., 85° C., 90° C. or the boiling point, i.e., the reflux temperature of the solvent used.

Preferably, the reaction time of the reaction 1-(v) can be appropriately selected within the range from half an hour to 48 hours, such as 0.5 hour, 1 hour, 3 hours, 5 hours, 8 hours, 10 hours, 12 hours, 15 hours, 18 hours, 20 hours, 23 hours, 25 hours, 28 hours, 30 hours, 33 hours, 35 hours, 38 hours, 40 hours, 44 hours or 48 hours.

Preparation Method 2

The compounds of general formula I of this invention can be prepared by an alternative method shown below, wherein $R_1$, $R_2$, $R_3$, $R_4$, Z, $Y_1$, $Y_2$, $W_1$, $W_2$, Hal and LG are defined above, unless otherwise specified.

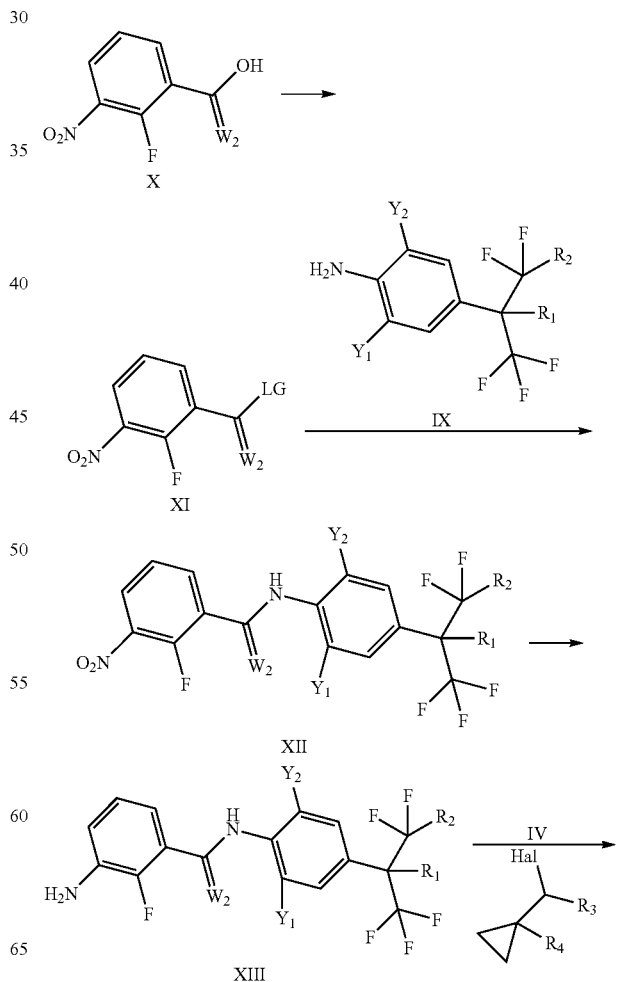

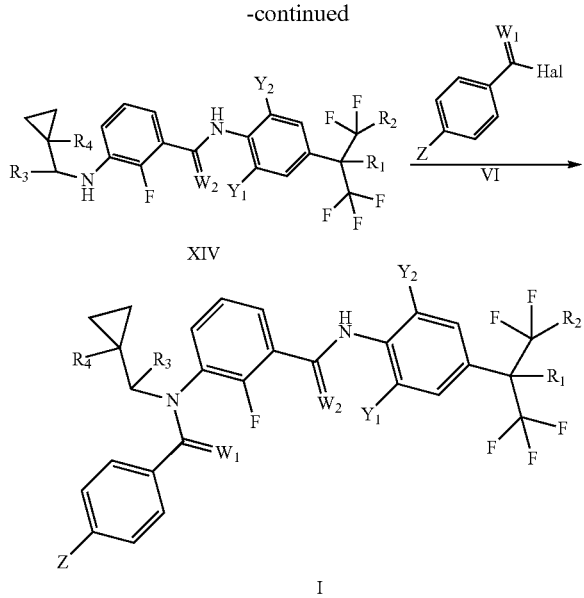

2-(i): Formula X→Formula XI

A compound represented by the general formula XI having a leaving group can be prepared by a well-known method reacting a compound represented by the general formula X with thionyl chloride, oxalyl chloride, phosphoryl chloride, phosphorus pentachloride, phosphorus trichloride, thionyl bromide, triphosgene, isopropyl trichloroformate or the like.

2-(ii): Formula XI+Formula IX→Formula XII

By reacting a compound represented by the general formula XI with a compound represented by the general formula IX according to the conditions described in 1-(v), a compound represented by the general formula XII can be prepared.

2-(iii): Formula XII→Formula XIII

An aromatic carboxamide derivative having an amino group represented by formula XIII can be derived from the aromatic carboxamide derivative having a nitro group represented by formula XII by means of a reduction reaction.

Such reduction is illustrated by a process using hydrogenation, a process using a metal compound (for example, stannous chloride) or a metal such as iron powder, zinc power and the like.

The hydrogenation reaction can be carried out in a suitable solvent in the presence of catalyst at atmospheric pressure or a higher pressure under a hydrogen atmosphere. Examples of the catalyst may include palladium catalysts such as palladium-carbon, cobalt catalysts, ruthenium catalysts, platinum catalysts and the like. Examples of the solvent may include alcohols such as methanol and ethanol; aromatic hydrocarbons such as benzene and toluene; chained or cyclic ethers such as ether and tetrahydrofuran; esters such as ethyl acetate.

Preferably, the hydrogenation reaction pressure can be appropriately selected within the range from 0.1 MPa to 10 MPa, such as 0.1 MPa, 0.5 MPa, 0.8 MPa, 1 MPa, 1.5 MPa, 2 MPa, 3 MPa, 4 MPa, 5 MPa, 6 MPa, 7 MPa, 8 MPa, 9 MPa or 10 MPa.

Preferably, the hydrogenation reaction temperature can be appropriately selected within the range from −20° C. to the boiling point of the solvent used, such as −20° C., −10° C., −5° C., 0° C., 5° C., 10° C., 15° C., 20° C., 25° C., 30° C., 35° C., 40° C., 45° C., 50° C., 60° C., 70° C., 75° C., 80° C. or the boiling point, i.e., the reflux temperature of the solvent used.

Preferably, the hydrogenation reaction time can be appropriately selected within the range from half an hour to 48 hours, such as 0.5 hour, 1 hour, 3 hours, 5 hours, 8 hours, 10 hours, 12 hours, 15 hours, 18 hours, 20 hours, 23 hours, 25 hours, 28 hours, 30 hours, 33 hours, 35 hours, 38 hours, 40 hours, 44 hours or 48 hours.

Preferably, the process using a metal compound or a metal is conducted in any one of methanol, ethanol, ethyl acetate or the mixture of at least two thereof.

Preferably, the metal compound is stannous chloride and the metal is any one of iron powder, zinc power or a combination of at least two thereof.

Preferably, the reaction temperature using a metal compound or a metal can be appropriately selected within the range from −10° C. to the boiling point of the solvent used, such as −10° C., −5° C., 0° C., 5° C., 10° C., 15° C., 20° C., 25° C., 30° C., 35° C., 40° C., 45° C., 50° C., 60° C., 70° C., 75° C., 80° C. or the boiling point, i.e., the reflux temperature of the solvent used.

Preferably, the reaction time using a metal compound or a metal can be appropriately selected within the range from half an hour to 48 hours, such as 0.5 hour, 1 hour, 3 hours, 5 hours, 8 hours, 10 hours, 12 hours, 15 hours, 18 hours, 20 hours, 23 hours, 25 hours, 28 hours, 30 hours, 33 hours, 35 hours, 38 hours, 40 hours, 44 hours or 48 hours.

2-(iv): Formula XIII+Formula IV→Formula XIV

By reacting a compound represented by the general formula XIII with a compound represented by the general formula IV according to the conditions described in 1-(i), a compound represented by the general formula XIV can be prepared.

2-(v): Formula XIV+Formula VI→Formula I

By reacting a compound represented by the general formula XIV with a compound represented by the general formula VI according to the conditions described in 1-(ii), a compound represented by the general formula I can be prepared.

On the other hand, this invention provides an intermediate representing by formula VIII for preparation of meta-carboxamido benzamide compounds of formula I.

Formula VIII

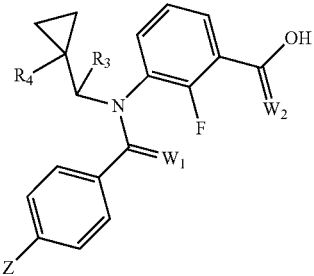

Wherein

Z is selected from the group consisting of H, F, Cl, Br, I, CN, $NO_2$, $C_1$-$C_6$ alkyl, $C_1$-$C_6$ haloalkyl, $C_1$-$C_6$alkoxyl, $C_1$-$C_6$haloalkoxyl, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl;

$R_3$ is selected from the group consisting of H, F, Cl, Br, I, $C_1$-$C_6$ alkyl, $C_1$-$C_6$ haloalkyl, $C_3$-$C_8$ cycloalkyl or $C_3$-$C_8$ halocycloalkyl; $R_4$ is selected from the group consisting of H or halogen; $W_1$ and $W_2$ are independently of each other O or S.

The preparation of intermediate VIII has been involved in the preparation method of the compounds of formula I above, and will not be repeated here.

Table 2 lists the representative compounds of intermediate VIII, but the present invention is not limited thereto.

TABLE 2

| No. | Z | $W_1$ | $W_2$ | $R_3$ | $R_4$ | Appearance |
|---|---|---|---|---|---|---|
| VIII1. | H | O | O | H | H | white solid |
| VIII2. | H | O | O | Me | H | white solid |
| VIII3. | H | O | O | c-Pr | H | white solid |
| VIII4. | H | O | O | Cl | H | |
| VIII5. | H | S | O | H | H | |
| VIII6. | H | O | S | H | H | |
| VIII7. | H | S | S | H | H | |
| VIII8. | CN | O | O | H | H | white solid |
| VIII9. | CN | O | O | Me | H | white solid |
| VIII10. | CN | O | O | c-Pr | H | white solid |
| VIII11. | $CF_3$ | O | O | H | H | white solid |
| VIII12. | $CF_3$ | O | O | Me | H | white solid |
| VIII13. | F | O | O | H | H | white solid |
| VIII14. | F | O | O | Me | H | white solid |
| VIII15. | Cl | O | O | H | H | white solid |
| VIII16. | Cl | O | O | Me | H | white solid |
| VIII17. | Br | O | O | H | H | white solid |
| VIII18. | Br | O | O | Me | H | white solid |
| VIII19. | $NO_2$ | O | O | H | H | |
| VIII20. | $NO_2$ | O | O | Me | H | |
| VIII21. | $OCF_3$ | O | O | H | H | white solid |
| VIII22. | $OCF_3$ | O | O | Me | H | |
| VIII23. | H | O | O | Me | Cl | |
| VIII24. | CN | O | O | Me | Cl | white solid |
| VIII25. | H | O | O | $CH_2Cl$ | H | |
| VIII26. | H | O | O | $CH_2F$ | H | |
| VIII27. | H | O | O | $CH_2Cl$ | Cl | |
| VIII28. | H | O | O | $CH_2F$ | Cl | |
| VIII29. | F | O | O | $CH_2Cl$ | H | |
| VIII30. | F | O | O | $CH_2F$ | H | |
| VIII31. | F | O | O | $CH_2Cl$ | Cl | |
| VIII32. | F | O | O | $CH_2F$ | Cl | |
| VIII33. | Cl | O | O | $CH_2Cl$ | H | |
| VIII34. | Cl | O | O | $CH_2F$ | H | |
| VIII35. | Cl | O | O | $CH_2Cl$ | Cl | |
| VIII36. | Cl | O | O | $CH_2F$ | Cl | |
| VIII37. | $CF_3$ | O | O | $CH_2Cl$ | H | |
| VIII38. | $CF_3$ | O | O | $CH_2F$ | H | |
| VIII39. | $CF_3$ | O | O | $CH_2Cl$ | Cl | |
| VIII40. | $CF_3$ | O | O | $CH_2F$ | Cl | |
| VIII41. | CN | O | O | $CH_2Cl$ | H | |
| VIII42. | CN | O | O | $CH_2F$ | H | |
| VIII43. | CN | O | O | $CH_2Cl$ | Cl | |
| VIII44. | CN | O | O | $CH_2F$ | Cl | |
| VIII45. | $OCF_3$ | O | O | $CH_2Cl$ | H | |
| VIII46. | $OCF_3$ | O | O | $CH_2F$ | H | |
| VIII47. | $OCF_3$ | O | O | $CH_2Cl$ | Cl | |
| VIII48. | $OCF_3$ | O | O | $CH_2F$ | Cl | |
| VIII49. | $MeS(O)_2$ | O | O | H | H | |
| VIII50. | $CF_3S(O)_2$ | O | O | H | H | |

Furthermore, this invention provides tautomers, enantiomers, non-enantiomers or salts of meta-carboxamido benzamide derivatives.

The tautomers, enantiomers, non-enantiomers or salts of meta-carboxamido benzamide derivatives have the same insecticidal activity as the meta-carboxamido benzamide derivatives, i.e., they have good insecticidal activity at low concentration and quick-acting property.

Furthermore, this invention provides use of the meta-carboxamido benzamide derivatives for controlling plant insects and nematodes in agriculture, forestry and horticulture.

The meta-carboxamido benzamide derivatives of this invention can effectively control pests of agriculture, forestry, horticulture, public health and nematodes, which are harmful to paddies, corns, wheats, potatoes, fruit trees, vegetables, other crops and flowering plants, etc.

The pests according to this invention contain lepidoptera, coleoptera, hemiptera, thysanoptera, diptera, orthoptera, homoptera, isoptera, hymenoptera, tetranychidae and nematodes, mosquitoes, flies, ants, etc.

Preferably, the pests according to this invention contain as follows but this invention is not limited thereto: *Helicoverpa armigera*(Hübner), *Plutella xylostella*(Linnaeus), *Spodoptera exigua*(Hübner), *Spodoptera litura*(Fabricius), *Pieris rapae* (Linne), *Chilo suppressalis*(Walker). *Tryporyza incertulas* (Walker), *Sesamia inferens* (Walker), *Spodoptera frugiperda* (J. E. Smith), *Cnaphalocrocis medinalis*(Guenee), *Chloethrips oryzae*(Wil.), *Frankliniella occidentalis*(Pergande), *Thrips fevas* (Schrank), *Thrips alliorum*(Priesner), *Myzus persicae* (Sulzer), *Aphis gossypii* (Glover), *Aphis craccivora* (Koch), *Aphis citricolavander* Goot, *Rhopalosiphum padi*, Flea beetle, Stinkbug, *Laodelphax striatellus*, *Nilaparvata lugens*(Stal), *Sogatella furcifera*, Termites, Flies and Mosquitoes, *Tetranychus cinnabarinus*, Citrus red mite.

The compounds of this invention can be broadly applied in the following categories: vegetables such as cucumber, loofah, watermelon, melon, pumpkin, hanging melon, spinach, celery, kale, cabbage, gourd, pepper, eggplant, tomato, shallot, ginger, garlic, leek, lettuce, kidney bean, cowpea, broad bean, radish, carrot, potato, yam; cereals such as wheat, barley, corn, rice, sorghum; fruits such as apple, pear, banana, citrus, grape, lychee, mango; flowering plants such as peony, rose, flamingo flower; oil crops such as peanuts, soybeans, rapeseed, sunflower, sesame; sugar-yielding crops such as sugar beets, sugarcane; other crops such as strawberries, potatoes, sweet potatoes, tobacco and tea; horticulture, forestry, home and public areas, etc. The usable scope of the meta-carboxamido benzamide derivatives according to this invention is not limited to the categories listed above.

On the other aspect, this invention provides an insecticidal composition comprising active ingredient(s) and acceptable carrier in agriculture, wherein the active ingredient(s) are the meta-carboxamido benzamide compounds described above, or the tautomers, enantiomers, diasteromers or salts thereof.

The composition of this invention can be used in form of a formulation, wherein the compounds represented by the general formula I are dissolved or dispersed in the carrier as active ingredients or they can be formulated to make them easier to disperse when they are used as pesticides The present disclosure relates to insecticide compositions, which can be made into a variety of formulation forms, such as, a wettable powder, a suspension concentrate, an aqueous emulsion or an emulsifiable concentrate, etc.

The present disclosure is designed to solve the problems of the related fields such as agriculture, forestry, public health, etc.

Preferably, in the insecticide composition, the weight percentage of the active component is 1-99%, such as 1%, 3%, 5%, 8%, 10%, 15%, 18%, 20%, 25%, 30%, 35%, 40%, 45%, 50%, 55%, 60%, 65%, 70%, 75%, 80%, 85%, 90%, 95% or 99%.

Preferably, the carrier acceptable in pesticide science includes surfactants.

The surfactants researched in present disclosure include ionic surfactants or nonionic surfactants.

The surfactants include emulsifiers, dispersants, or wetting agents. The emulsifiers researched in present disclosure include polyoxyethylene fatty acid ester, polyoxyethylene aliphatic alcohol ether, fatty amine polyoxyethylene ether and commercially available emulsifiers, such as pesticide emulsifier 2201B, 0203B, 100#, 500#, 600#, 600-2#, 1601, 2201, NP-10, NP-15, 507#, OX-635, OX-622, OX-653, OX-667, 36# and the like. The dispersants researched in present disclosure include sodium lignin sulfonate, nekal, calcium lignin sulfonate, methylnaphthalene sulfonate formaldehyde condensate and so on. The wetting agents researched in present disclosure include sodium lauryl sulfate, sodium dodecyl benzene sulfonate, sodium alkyl naphthalene sulfonate and the like.

Preferably, the carriers acceptable in pesticide science include solid carriers and/or liquid carriers.

Preferably, the solid carriers researched in present disclosure include natural or synthetic clays and silicates (for example, natural silica, diatomite); magnesium silicate (for example, talc); magnesium aluminum silicate (for example, kaolinite, kaolin, montmorillonite and mica); precipitated silica, calcium carbonate, light calcium carbonate, calcium sulfate, limestone, sodium sulfate; amine salt (for example, ammonium sulfate, hexamethylene diamine). The liquid carriers researched in present disclosure include water and organic solvents. When water is used as a solvent or diluent, organic solvents can also be used as additives or antifreeze additives. The suitable organic solvents in present disclosure include aromatic hydrocarbon (for example, benzene, xylene, toluene and the like); chlorinated hydrocarbon (for example, chlorobenzene, chloroethylene, trichloromethane, dichloromethane and the like); aliphatic hydrocarbon (for example, petroleum fractions, cyclohexane, light mineral oil and the like); alcohols (for example, isopropanol, butanol, glycol, glycerol and cyclohexanol and the like), their ethers and esters; ketones (for example, acetone, cyclohexanone); dimethylformamide and N-methylpyrrolidone.

During the preparation of the pesticide composition, the active ingredient(s) may be mixed with the liquid and/or solid carriers. Surfactants (such as emulsifiers, dispersants, stabilizers, wetting agents) and other auxiliaries (such as adhesives, defoaming agents, oxidants, etc.) may be added as well.

On the other aspect, this invention provides a method for controlling insects, wherein an effective concentration of the meta-carboxamido benzamide compounds, or the tautomers, enantiomers, diasteromers or salts thereof, or the composition described above will be used to the insects to be controlled or to their habitat.

Preferably, the effective concentration is within a range from 10 g/ha to 1000 g/ha, such as 10 g/ha, 20 g/ha, 50 g/ha, 80 g/ha, 100 g/ha, 120 g/ha, 150 g/ha, 180 g/ha, 200 g/ha, 250 g/ha, 300 g/ha, 350 g/ha, 400 g/ha, 450 g/ha, 500 g/ha, 600 g/ha, 700 g/ha, 800 g/ha, 900 g/ha or 1000 g/ha. More preferably, the effective concentration is within a range from 25 g/ha to 500 g/ha.

The composition of this invention can be used to the insects and their habitat in form of a formulation. The compounds represented by the general formula I are dissolved or dispersed in the carrier as an active ingredient or they can be formulated to make them easier to disperse when they are used as pesticides. These compounds can be formulated into such as various liquid formulations, emulsifiable concentrates, suspensions, aqueous suspensions, microemulsions, emulsions, aqueous emulsions, powder, wettable powder, soluble powder, granules, aqueous dispersible granules or capsule.

For certain applications, for example, in agriculture, one or more additional agents, such as insecticides, fungicides, herbicides, plant growth regulators or fertilizers, can be added into the insecticide composition of this invention, so as to obtain additional advantages and effects.

Comparing with the prior art, this invention has following benefits:

The meta-carboxamido benzamide derivatives of this invention are significantly effective for controlling the pests and nematodes in agriculture, forestry and public health. They have excellent insecticidal activity at low concentration, which can be exerted after one day of application, and excellent insecticidal activity can be achieved on the third day, with good quick-acting property. The good insecticidal activity at low concentration of the meta-carboxamido benzamide derivatives of this invention can reduce the damage of pesticide application to plant and human beings and the residue of pesticide, so they are more conducive to environmental protection. The methods for production are also simple and efficient, and the mass production can be easily realized. Thus the compounds and the compositions of this invention have a wide application prospect.

EXAMPLES

Representative Examples of this invention will be described in the following Examples. Those skilled in the art should understand that the examples herein are only illustrative, and this invention is not limited thereto. SGC represents silica gel column chromatography in the following examples.

Preparation Examples

Example 1: Preparation of N-(2-bromo-4-(perfluoropropan-2-yl)-6-(trifluoromethyl)phenyl)-3-(N-(cyclopropylmethyl)benzamido)-2-fluorobenzamide (Compound No. 4)

Step 1: Preparation of methyl 3-((cyclopropylmethyl)amino)-2-fluorobenzoate

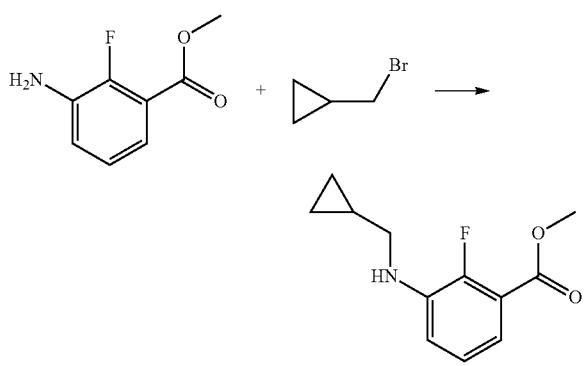

To the solution of methyl 3-amino-2-fluorobenzoate (20 g, 118.23 mmol) in anhydrous DMF (200 mL) was added potassium carbonate (21.24 g, 153.70 mmol) and (bromomethyl) cyclopropane (20.75 g, 153.70 mmol). Then the mixture was heated and refluxed for 16 hours. TLC showed the reaction was finished. The reaction mixture was extracted with ethyl acetate (100 mL) and H$_2$O (200 mL). The organic layer was washed with saturated brine, and then dried over anhydrous magnesium sulphate. The solvent was evaporated under reduced pressure and the obtained residue was purified by SGC (eluent: petroleum ether:ethyl acetate=10:1) to obtain 13 g (yield 49.390%) of the target compound as light yellow liquid.

Step 2: Preparation of methyl 3-(N-(cyclopropylmethyl)benzamido)-2-fluorobenzoate

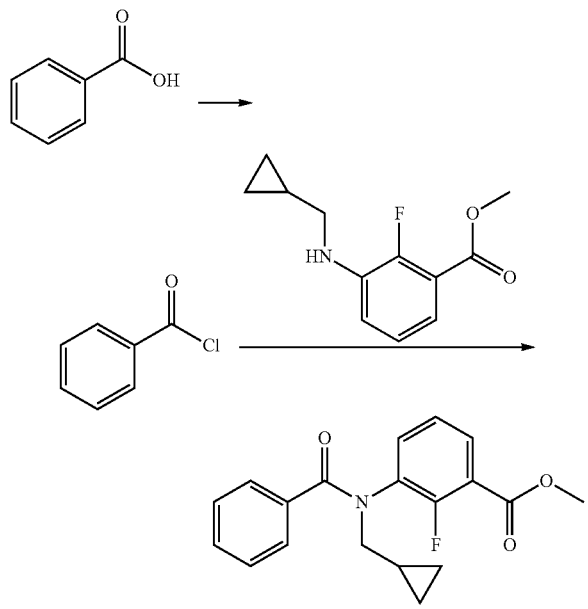

Thionyl chloride (31.99 g, 268.9 mmol) was added to benzoic acid (6.67 g, 53.78 mmol) in toluene (50 mL), and the mixture was heated and refluxed for 2 hours. After the solvent was removed by distillation, the coarse product benzoyl chloride in THF (30 mL) was used for the next step without further purification. To the solution of methyl 3-((cyclopropylmethyl)amino)-2-fluorobenzoate (10.00 g, 44.82 mmol) in anhydrous THF (100 mL) was added pyridine (4.25 g, 53.78 mmol) and benzoyl chloride. Then the mixture was stirred at room temperature for 4 hours. TLC showed the reaction was completed. To the mixture was added ethyl acetate (50 mL). The organic layer was washed with 2 M hydrochloric acid and saturated brine, and then dried over anhydrous magnesium sulphate. The solvent was evaporated under reduced pressure and the obtained residue was purified by SGC (eluent: petroleum ether:ethyl acetate=8:1) to obtain 13 g (yield 88.70%) of the target compound as colorless liquid.

Step 3: Preparation of 3-(N-(cyclopropylmethyl)benzamido)-2-fluorobenzoic acid

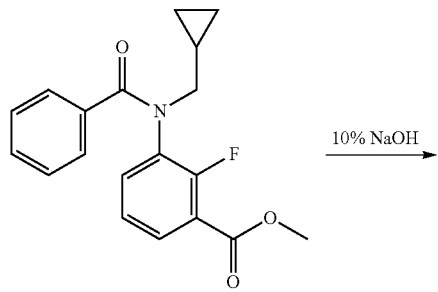

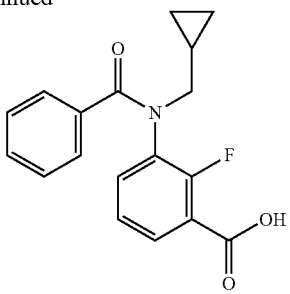

Methyl 3-(N-(cyclopropylmethyl)benzamido)-2-fluorobenzoate (13.00 g, 40.88 mmol) was dissolved in methanol (100 mL), 10% sodium hydroxide aqueous solution (6.54 g, 163.52 mmol, 65.4 mL) was added and the reaction mixture was stirred at room temperature for 2 hours. TLC showed the reaction was completed. After the solvent was removed by distillation, the coarse product was dissolved in H$_2$O (100 mL) and extracted with ethyl acetate (50 mL). The pH of the aqueous phase was acidified by the addition of 2M hydrochloric acid to 7 and extracted with ethyl acetate (100 mL). The organic layer was washed with saturated brine, dried over anhydrous magnesium sulphate and evaporated under reduced pressure to obtain 12 g (yield 93.82%) of the target compound as colorless liquid, which converts to white solid after standing overnight.

Step 4: Preparation of N-(2-bromo-4-(perfluoropropan-2-yl)-6-(trifluoromethyl)phenyl)-3-(N-(cyclopropylmethyl)benzamido)-2-fluorobenzamide

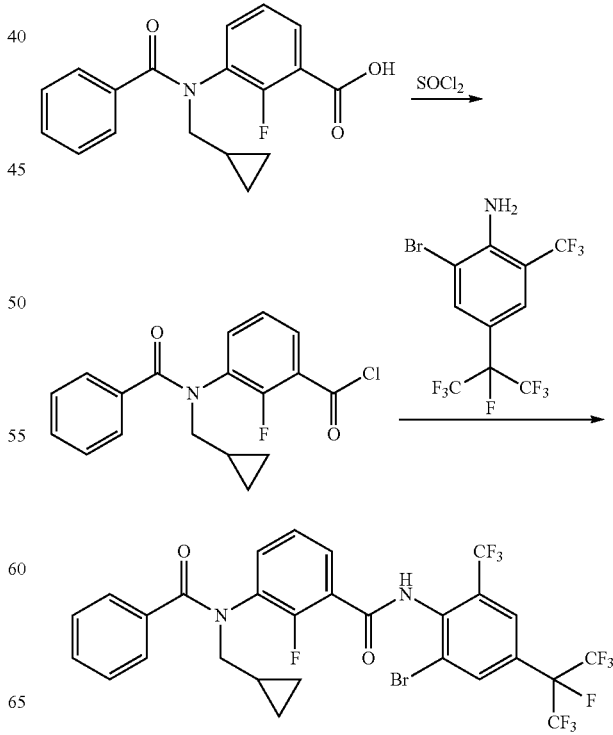

To the solution of 3-(N-(cyclopropylmethyl)benzamido)-2-fluorobenzoic acid (0.40 g, 1.28 mmol) in toluene (6 mL) was added thionyl chloride (0.75 g, 6.40 mmol). Then the mixture was heated and refluxed for 2 hours. After the solvent was removed by distillation, the coarse product 3-(N-(cyclopropylmethyl)benzamido)-2-fluorobenzoyl chloride in THF (3 mL) was used for the next step without further purification, 2-bromo-4-(perfluoropropan-2-yl)-6-(trifluoromethyl)aniline (0.52 g, 1.28 mmol) was charged to anhydrous THF (4 mL) and cooled to −70° C. under a nitrogen atmosphere, 2.0 M lithium diisopropyl amide hexane solution (0.77 mL, 1.54 mmol) was added dropwise thereto. After 5 min 3-(N-(cyclopropylmethyl)benzamido)-2-fluorobenzoyl chloride dissolved in THF (3 mL) was added dropwise thereto and the mixture was stirred at −70° C. for 30 min and at room temperature for another 30 min. TLC showed the reaction was finished. The reaction mixture was diluted with H$_2$O (20 mL) and extracted with ethyl acetate (20 mL). The organic layer was washed with saturated brine and dried over anhydrous magnesium sulphate. The solvent was evaporated under reduced pressure and the obtained residue was purified by SGC (eluent: petroleum ether:ethyl acetate=3:1) to obtain 0.25 g (yield 27.84%) of the target compound.

For Compound No. 4: $^1$H NMR (CDCl$_3$-d, 400 MHz), δ[ppm]: 8.15 (d, J=2.1 Hz, 1H), 8.03 (br s, 2H), 7.92 (d, J=2.1 Hz, 1H), 7.55 (br s, 1H), 7.35-7.21 (m, 5H), 3.84 (d, J=93.6 Hz, 2H), 1.14 (br s, 1H), 0.59-0.40 (m, 2H), 0.20 (d, J=42.2 Hz, 2H).

Example 2: Preparation of

N-(2-bromo-4-(perfluoropropan-2-yl)-6-(trifluoromethyl)phenyl)-3-(4-cyano-N-(cyclopropylmethyl)benzamido)-2-fluorobenzamide (Compound No. 23)

Step 1: Preparation of methyl 3-(4-cyano-N-(cyclopropylmethyl)benzamido)-2-fluorobenzoate

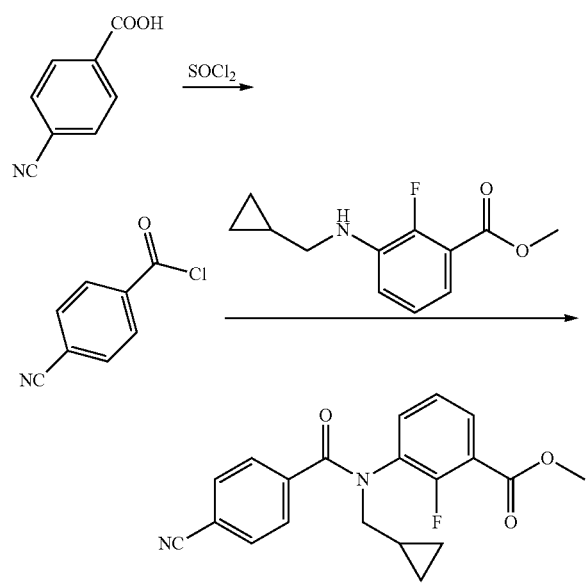

Thionyl chloride (3.2 g, 26.9 mmol) was added to 4-cyanobenzoic acid (0.80 g, 5.38 mmol) in toluene (6 mL). The mixture was heated and refluxed for 2 hours. After the solvent was removed by distillation, the coarse product 4-cyanobenzoyl chloride was dissolved in THF (3 mL) and used for the next step. To the solution of 3-((cyclopropylmethyl)amino)-2-fluorobenzoate (1.0 g, 4.48 mmol) in anhydrous THF (6 mL) was added triethylamine (0.74 g, 5.38 mmol) and 4-cyanobenzoyl chloride THF solution dropwise. The mixture was stirred at room temperature for 4 hours. TLC showed the reaction was completed. The mixture was diluted with H$_2$O (20 mL) and extracted with ethyl acetate (20 mL) and. The organic layer was washed with saturated brine dried over anhydrous magnesium sulphate and evaporated under reduced pressure. The residue was purified by SGC (eluent: petroleum ether:ethyl acetate=3:1) to obtain 1.40 g (yield 88.83%) of the target compound.

Step 2: Preparation of 3-(4-cyano-N-(cyclopropylmethyl)benzamido)-2-fluorobenzoic acid

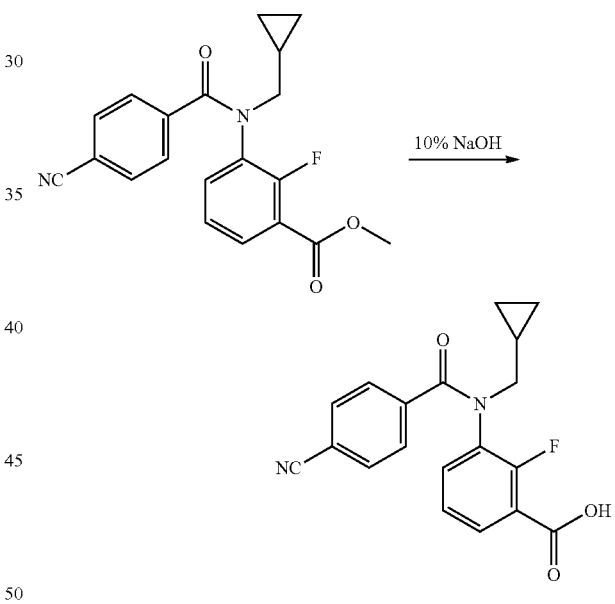

Methyl 3-(4-cyano-N-(cyclopropylmethyl)benzamido)-2-fluorobenzoate (1.40 g, 3.96 mmol) was dissolved in methanol (20 mL), 10% sodium hydroxide aqueous solution (0.63 g, 15.86 mmol, 6.3 mL) was added and the reaction mixture was stirred at room temperature for 2 hours. TLC showed the reaction was completed. After the solvent was removed by distillation, the residue was dissolved in H$_2$O (20 mL) and extracted with ethyl acetate (10 mL). The organic phase was dropped. The pH of the aqueous phase was acidified to 7 by 2M hydrochloric acid and extracted with ethyl acetate (10 mL). The organic layer was washed with saturated brine, dried over anhydrous magnesium sulphate and evaporated under reduced pressure to obtain 1.30 g (yield 96.79%) of the target compound as a white solid.

23

Step 3: Preparation of N-(2-bromo-4-(perfluoropropan-2-yl)-6-(trifluoromethyl)phenyl)-3-(4-cyano-N-(cyclopropylmethyl)benzamido)-2-fluorobenzamide

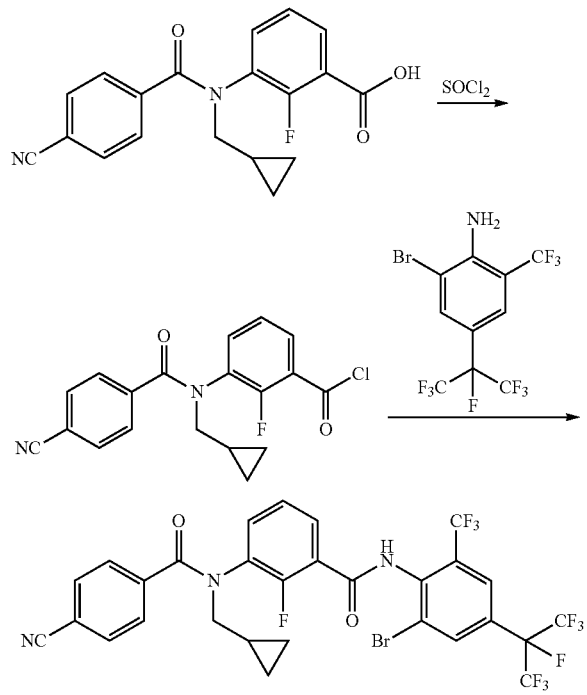

To 3-(4-cyano-N-(cyclopropylmethyl)benzamido)-2-fluorobenzoic acid (0.75 g, 2.22 mmol) in toluene (6 mL) was added thionyl chloride (1.31 g, 11.10 mmol). The mixture was heated and refluxed for 2 hours. After the solvent was removed by distillation, the coarse product 3-(4-cyano-N-(cyclopropylmethyl)benzamido)-2-fluorobenzoyl chloride was dissolved in THF (3 mL) and used for the next step. 2-Bromo-4-(perfluoropropan-2-yl)-6-(trifluoromethyl)aniline (0.90 g, 2.22 mmol) was charged to anhydrous THF (4 mL) and cooled to −70° C. under a nitrogen atmosphere. 2.0 M lithium diisopropyl amide hexane solution (1.30 mL, 2.66 mmol) was added dropwise thereto. After 5 min 3-(4-cyano-N-(cyclopropylmethyl)benzamido)-2-fluorobenzoyl chloride THF solution was added dropwise. The mixture was stirred at −70° C. for 30 min and at room temperature for another 30 min. TLC showed the reaction was finished. The reaction mixture was diluted with saturated NH$_4$Cl solution (20 mL) and extracted with ethyl acetate (20 mL). The organic layer was washed with saturated brine, dried over anhydrous magnesium sulphate and evaporated under reduced pressure. The residue was purified by SGC (eluent: petroleum ether:ethyl acetate=3:1) to obtain 0.24 g (yield 14.91%) of the target compound.

For Compound No. 23: $^1$H NMR (CDCl$_3$-d, 400 MHz), δ[ppm]: 8.14 (d, J=2.0 Hz, 1H), 8.12-7.94 (m, 2H), 7.91 (t, J=1.4 Hz, 1H), 7.58-7.39 (m, 4H), 7.32 (t, J=7.9 Hz, 1H), 3.81 (dd, J=76.0, 18.8 Hz, 2H), 1.11 (br s, 1H), 0.5 (br s, 2H), 0.20 (d, J=36.7 Hz, 2H).

24

Example 3: Preparation of N-(2-bromo-4-(perfluoropropan-2-yl)-6-(trifluoromethyl)phenyl)-3-(N-(cyclopropylmethyl)-4-(trifluoromethyl)benzamido)-2-fluorobenzamide (Compound No. 37)

(1) To 3-(N-(cyclopropylmethyl)-4-(trifluoromethyl)benzamido)-2-fluorobenzoic acid (0.45 g, 1.12 mmol) in toluene (6 mL) was added thionyl chloride (0.67 g, 5.60 mmol). The mixture was heated and refluxed for 2 hours. After the solvent was removed by distillation, the coarse 3-(N-(cyclopropylmethyl)-4-(trifluoromethyl)benzamido)-2-fluorobenzoyl chloride was dissolved in THF (3 mL) and used for the next step.

(2) 2-Bromo-4-(perfluoropropan-2-yl)-6-(trifluoromethyl)aniline (0.46 g, 1.12 mmol) was charged to anhydrous THF (4 mL) and cooled to −70° C. under a nitrogen atmosphere. 2.0 M lithium diisopropyl amide hexane solution (0.70 mL, 1.42 mmol) was added dropwise thereto. After 5 min 3-(N-(cyclopropylmethyl)-4-(trifluoromethyl)benzamido)-2-fluorobenzoyl chloride THF solution was added dropwise. The mixture was stirred at −70° C. for 30 min and at room temperature for another 30 min. TLC showed the reaction was finished. The reaction mixture was diluted with H$_2$O (20 mL) and extracted with ethyl acetate (20 mL). The organic layer was washed with saturated brine, dried over anhydrous magnesium sulphate and evaporated under reduced pressure. The residue was purified by SGC (eluent: petroleum ether:ethyl acetate=3:1) to obtain 0.11 g (yield 13.75%) of the target compound.

For Compound No. 37: $^1$H NMR (CDCl$_3$-d, 400 MHz), δ[ppm]: 8.21-7.79 (m, 4H), 7.66-7.28 (m, 5H), 3.85 (d, J=104.7 Hz, 2H), 1.12 (br s, 1H), 0.51 (br s, 2H), 0.20 (d, J=42.7 Hz, 1H).

Example 4: Preparation of N-(2-bromo-4-(perfluoropropan-2-yl)-6-(trifluoromethyl)phenyl)-3-(4-chloro-N-(cyclopropylmethyl)benzamido)-2-fluorobenzamide (Compound No. 41)

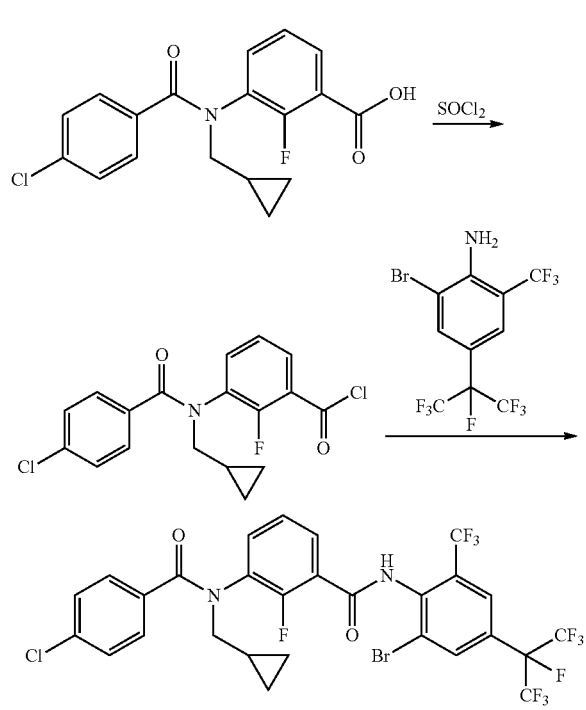

(1) To 3-(4-chloro-N-(cyclopropylmethyl)benzamido)-2-fluorobenzoic acid (0.60 g, 1.76 mmol) in toluene (6 mL) was added thionyl chloride (1.04 g, 8.80 mmol). The mixture was heated and refluxed for 2 hours. After the solvent was removed by distillation, the coarse 3-(4-chloro-N-(cyclopropylmethyl)benzamido)-2-fluorobenzoyl chloride was dissolved in THF (3 mL) and used for the next step.

(2) 2-Bromo-4-(perfluoropropan-2-yl)-6-(trifluoromethyl)aniline (0.72 g, 1.76 mmol) was charged to anhydrous THF (4 mL) and cooled to −70° C. under a nitrogen atmosphere. 2.0 M lithium diisopropyl amide hexane solution (1.05 mL, 2.11 mmol) was added dropwise thereto. After 5 min 3-(4-chloro-N-(cyclopropylmethyl)benzamido)-2-fluorobenzoyl chloride THF solution was added dropwise. The mixture was stirred at −70° C. for 30 min and at room temperature for 30 another min. TLC showed the reaction was finished. The reaction mixture was diluted with $H_2O$ (20 mL) and extracted with ethyl acetate (20 mL). The organic layer was washed with saturated brine, dried over anhydrous magnesium sulphate and evaporated under reduced pressure. The residue was purified by SGC (eluent: petroleum ether: ethyl acetate=3:1) to obtain 0.15 g (yield 11.63%) of the target compound.

For Compound No. 41: $^1H$ NMR ($CDCl_3$-d, 400 MHz), δ[ppm]: 8.18-7.84 (m, 4H), 7.53 (t, J=7.7 Hz, 1H), 7.37-7.07 (m, 4H), 3.81 (d, J=85.0 Hz, 2H), 1.11 (br s, 1H), 0.49 (br s, 2H), 0.17 (d, J=32.1 Hz, 2H).

Example 5: Preparation of N-(2-bromo-4-(perfluoropropan-2-yl)-6-(trifluoromethyl)phenyl)-3-(N-(cyclopropylmethyl)-4-fluorobenzamido)-2-fluorobenzamide (Compound No. 62)

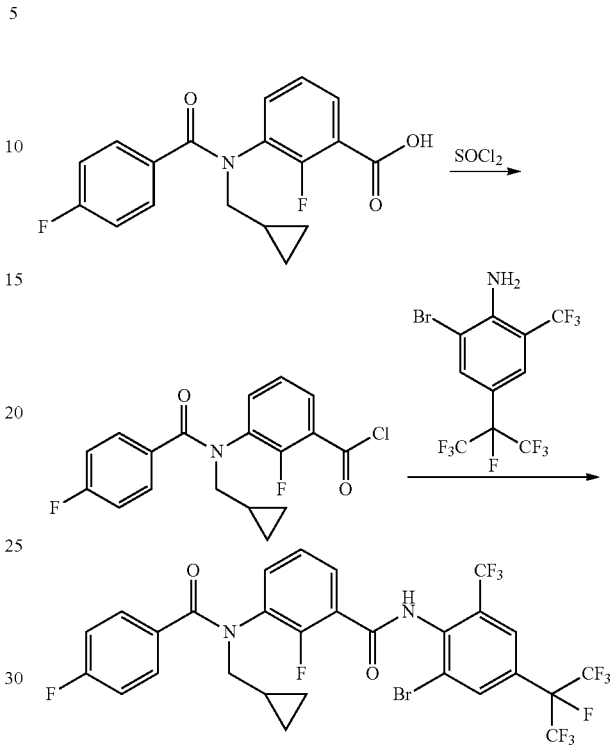

To 3-(N-(cyclopropylmethyl)-4-fluorobenzamido)-2-fluorobenzoic acid (2.20 g, 6.67 mmol) in toluene (20 mL) was added thionyl chloride (3.97 g, 33.35 mmol l). The mixture was heated and refluxed for 2 hours. After the solvent was removed by distillation, the coarse 3-(N-(cyclopropylmethyl)-4-fluorobenzamido)-2-fluorobenzoyl chloride was used for the next step.

2-Bromo-4-(perfluoropropan-2-yl)-6-(trifluoromethyl) aniline (3.26 g, 7.99 mmol), N,N-Diisopropyl-ethylamin (1.72 g, 13.30 mmol) and 4-N,N-dimethylaminopyridine (0.33 g, 2.69 mmol) was added to 3-(N-(cyclopropylmethyl)-4-fluorobenzamido)-2-fluorobenzoyl chloride. The mixture was heated at 120° C. for 2 hours. The reaction mixture was dissolved in $H_2O$ (20 mL) and extracted with ethyl acetate (20 mL). The organic layer was washed with saturated brine, dried over anhydrous magnesium sulphate and evaporated under reduced pressure. The residue was purified by SGC (eluent: petroleum ether:ethyl acetate=3:1) to obtain 1.80 g (yield 37.5%) of the target compound.

For Compound No. 62: $^1H$ NMR ($CDCl_3$-d, 400 MHz), δ[ppm]: 10.56 (s, 1H), 8.41 (s, 1H), 7.95 (s, 1H), 7.70-7.56 (m, 2H), 7.38-7.32 (m, 3H), 7.09 (br s, 2H), 3.69 (br s, 2H), 1.03-1.01 (m, 1H), 0.41-0.39 (m, 2H), 0.08-0.06 (m, 2H).

Example 6: Preparation of N-(2-bromo-4-(perfluoropropan-2-yl)-6-(trifluoromethyl)phenyl)-3-(N-(1-cyclopropylethyl)benzamido)-2-fluorobenzamide (Compound No. 8)

Step 1: Preparation of methyl 3-((1-cyclopropylethyl)amino)-2-fluorobenzoate To a solution of methyl 3-amino-2-fluorobenzoate (2.00 g, 11.82 mmol) in anhydrous 1,2-dichloroethane (65 mL) was added 1-cyclopropylethan-1-one (2.98 g, 35.47 mmol), trifluoroacetic acid (8.08 g, 70.92 mmol) and sodium triacetoxyborohydride (7.51 g, 35.47 mmol) at room temperature. The mixture was heated at 45° C. for 1 hour. When TLC showed the reaction was finished, the mixture was diluted with saturated NaHCO₃ solution (50 mL) and extracted with dichloromethane (80 mL). The organic layer was washed with saturated brine, dried over anhydrous magnesium sulphate and evaporated under reduced pressure. The residue was purified by SGC (eluent: petroleum ether:ethyl acetate=10:1) to obtain 1.50 g (yield 53.5%) of the target compound as colorless oil.

Step 2: Preparation of methyl 3-(N-(1-cyclopropylethyl)benzamido)-2-fluorobenzoate Thionyl chloride (6.27 g, 52.68 mmol) was added to benzoic acid (1.54 g, 12.64 mmol) in toluene (15 mL). The mixture was heated and refluxed for 2 hours. After the solvent was removed by distillation, the coarse benzoyl chloride was dissolved in THF (5 mL) and used for the next step.

To a solution of methyl 3-((1-cyclopropylethyl)amino)-2-fluorobenzoate (2.50 g, 10.54 mmol) in anhydrous THF (15 mL) was added triethylamine (1.60 g, 15.80 mmol) and benzoyl chloride THF solution. The mixture was heated and stirred at 80° C. for 6 hours. TLC showed the reaction was completed. The mixture was diluted with H₂O (50 mL) and extracted with ethyl acetate (60 mL). The organic layer was washed with saturated brine, dried over anhydrous magnesium sulphate and evaporated under reduced pressure. The residue was purified by SGC (eluent: petroleum ether:ethyl acetate=10:1) to obtain 1.03 g (yield 28.6%) of the target compound as a yellow solid.

Step 3: Preparation of 3-(N-(1-cyclopropylethyl) benzamido)-2-fluorobenzoic acid Methyl 3-(N-(1-cyclopropylethyl)benzamido)-2-fluorobenzoate (1.00 g, 2.93 mmol) was dissolved in methanol (10 mL). 10% sodium hydroxide aqueous solution (0.46 g, 11.72 mmol, 4.6 mL) was added and the reaction mixture was stirred at room temperature for 2 hours. TLC showed the reaction was completed. After the solvent was removed by distillation, the residue was dissolved in H₂O (20 mL) and extracted with ethyl acetate (10 mL). The organic phase was dropped. The pH of the aqueous phase was acidified to 3 by the addition of 2M hydrochloric acid. Then the mixture was extracted with ethyl acetate (10 mL). The organic layer was washed with saturated brine, dried over anhydrous magnesium sulphate and evaporated under reduced pressure to obtain 0.60 g (yield 62.6%) of the target compound.

Step 4: Preparation of N-(2-bromo-4-(perfluoropropan-2-yl)-6-(trifluoromethyl)phenyl)-3-(N-(1-cyclopropylethyl)benzamido)-2-fluorobenzamide To 3-(N-(1-cyclopropylethyl)benzamido)-2-fluorobenzoic acid (0.60 g, 1.83 mmol) in toluene (6 mL) was added thionyl chloride (1.09 g, 9.16 mmol). The mixture was heated and refluxed for 2 hours. After the solvent was removed by distillation, the coarse 3-(N-(1-cyclopropylethyl)benzamido)-2-fluorobenzoyl chloride was dissolved in THF (2 mL) and used for the next step.

2-Bromo-4-(perfluoropropan-2-yl)-6-(trifluoromethyl) aniline (0.75 g, 1.83 mmol) was charged to anhydrous THF (6 mL) and cooled to −70° C. under a nitrogen atmosphere. 2.0 M lithium diisopropyl amide hexane solution (1.10 mL, 2.20 mmol) was added dropwise thereto. After 5 min 3-(N-(1-cyclopropylethyl)benzamido)-2-fluorobenzoyl chloride THF solution was added dropwise. The mixture was stirred at −70° C. for 30 min and at room temperature for another 30 min. When TLC showed the reaction was finished, the reaction mixture was diluted with H₂O (20 mL) and extracted with ethyl acetate (20 mL). The organic layer was washed with saturated brine, dried over anhydrous magnesium sulphate and evaporated under reduced pressure. The residue was purified by SGC (eluent: petroleum ether:ethyl acetate=5:1) to obtain 0.23 g (yield 17.5%) of the target compound as a yellow solid.

For Compound No. 8: ¹H NMR (CDCl₃-d, 400 MHz), δ[ppm]: 8.19 (s, 1H), 8.05-7.95 (m, 1H), 7.89 (s, 1H), 7.77-7.73 (m, 1H), 7.56-7.52 (m, 1H), 7.28-7.11 (m, 6H), 4.26-4.23 (m, 1H), 1.63 (br s, 2H), 1.51 (br s, 1H), 0.89-0.40 (m, 5H).

In addition to the compounds described in the examples, other compounds in Table 1 can be prepared according to the similar methods as described in examples 1-6. Herein below, Table 3 shows the NMR data of some compounds prepared according to this invention examples 1-6. The ¹H NMR chemical shift values shown therein are based on tetramethylsilane as an internal standard substance unless specified otherwise.

TABLE 3

| Compound No. | ¹H NMR (CDCl₃, ppm) |
|---|---|
| 22 | 400 MHz, DMSO-d₆, δ[ppm]: 10.44 (s, 1H), 8.40 (s, 1H), 7.96-7.93 (m, 2H), 7.64-7.58 (m, 1H), 7.34-7.22 (m, 6H), 3.56 (br s, 1H), 1.06-1.03 (m, 1H), 0.84-0.80 (m, 1H), 0.65-0.38 (m, 8H). |
| 24 | 400 MHz, DMSO-d₆, δ[ppm]: 10.50 (s, 1H), 8.19 (s, 1H), 7.82-7.35 (m, 8H), 3.75 (d, J = 86.5 Hz, 2H), 3.57(s, 3H), 0.87-0.84 (m, 1H), 0.43-0.13 (m, 4H). |
| 26 | 400 MHz, DMSO-d₆, δ[ppm]: 10.51 (d, J = 27.1 Hz, 1H), 8.54-8.35 (m, 1H), 7.95 (s, 1H), 7.86-7.51 (m, 4H), 7.51-7.20 (m, 3H), 4.03 (q, J = 7.1 Hz, 1H), 1.30-1.19 (m, 3H), 0.93-0.23 (m, 5H). |
| 32 | 400 MHz, DMSO-d₆, δ[ppm]: 10.45 (s, 1H), 8.41 (s, 1H), 7.95 (s, 1H), 7.84-7.80 (m, 1H), 7.71-7.61 (m, 3H), 7.45-7.35 (m, 3H), 3.59-3.55 (m, 1H), 1.10 (br s, 1H), 0.85-0.80 (m, 1H), 0.67-0.40(m, 8H). |
| 38 | ¹H NMR (400 MHz, DMSO-d₆), δ [ppm]: 10.46 (s, 1H), 8.19 (s, 1H), 7.78 (d, J = 25.9 Hz, 3H), 7.56 (d, J = 40.0 Hz, 4H), 7.36 (s, 1H), 3.76 (d, J = 36.8 Hz, 2H), 3.57 (s, 3H), 0.93-0.79 (m, 1H), 0.43 (s, 2H), 0.13 (d, J = 30.4 Hz, 2H). |

TABLE 3-continued

| Compound No. | $^1$H NMR (CDCl$_3$, ppm) |
|---|---|
| 39 | 400 MHz, DMSO-d$_6$, δ[ppm]: 10.44 (d, J = 30.3 Hz, 1H), 8.41 (s, 1H), 7.94 (s, 1H), 7.80-7.73(m, 1H), 7.70-7.27 (m, 6H), 4.09-4.07 (m, 1H), 1.50-1.15 (m, 3H), 0.95-0.19 (m, 5H). |
| 43 | 400 MHz, DMSO-d$_6$ δ[ppm]: 10.55 (s, 1H), 8.20 (s, 1H), 7.82 (s, 1H), 7.70-7.59 (m, 2H), 7.32 (br s, 5H), 3.71 (br s, 2H), 3.57 (s, 3H), 1.03 (br s, 1H), 0.42 (br s, 2H), 0.09 (br s, 2H). |
| 44 | 400 MHz, DMSO-d$_6$, δ[ppm]: 10.53 (d, J = 25.5 Hz, 1H), 8.46-8.37 (m, 1H), 7.98-7.91 (m, 1H), 7.80-7.55 (m, 2H), 7.32 (d, J = 33.8 Hz, 5H), 4.03 (q, J = 7.1 Hz, 1H), 1.46-1.15 (m, 3H), 0.90-0.18 (m, 5H). |
| 46 | 400 MHz, CDCl$_3$-d, δ[ppm]: 8.13 (d, J = 2.0 Hz, 1H), 8.05 (t, J = 7.6 Hz, 1H), 7.90 (s, 1H), 7.54 (t, J = 7.8 Hz, 1H), 7.32 (d, J = 9.7 Hz, 2H), 7.21 (t, J = 6.7 Hz, 3H), 3.81 (d, J = 87.9 Hz, 2H), 1.10 (br s, 1H), 0.50 (br s, 2H), 0.18 (d, J = 35.8 Hz, 2H). |
| 47 | 400 MHz, CDCl$_3$-d, δ[ppm]: 8.36 (d, J = 2.1 Hz, 1H), 8.26-7.91 (m, 3H), 7.59 (s, 1H), 7.44-7.29 (m, 3H), 7.23 (br s, 2H), 4.00 (br s, 1H), 3.69 (br s, 1H), 1.14 (br s, 1H), 0.52 (br s, 2H), 0.21 (d, J = 56.0 Hz, 2H). |
| 49 | 400 MHz, DMSO-d$_6$ δ[ppm]: 10.54 (s, 1H), 8.20 (s, 1H), 7.82 (s, 1H), 7.70-7.59 (m, 2H), 7.51-7.18 (m, 5H), 3.70 (br s, 2H), 3.57 (s, 3H), 1.02-0.97 (m, 1H), 0.41 (d, J = 8.1 Hz, 2H), 0.17-0.02 (m, 2H). |
| 50 | 400 MHz, DMSO-d$_6$, δ[ppm]: 10.53 (d, J = 34.0 Hz, 1H), 8.41 (s, 1H), 7.95 (s, 1H), 7.76-7.62 (m, 2H), 7.42-7.20 (s, 5H), 4.03-3.97 (m, 1H), 1.39-1.21 (m, 3H), 0.85-0.24 (m, 5H). |
| 52 | 400 MHz, DMSO-d$_6$, δ[ppm]: 10.43 (s, 1H), 7.95 (br s, 2H), 7.60-7.54 (m, 4H), 7.26 (br s, 2H), 7.01 (br s, 1H), 3.63 (br s, 2H), 0.93 (br s, 1H), 0.32 (d, J = 8.1 Hz, 2H), 0.04 (br s, 2H). |
| 53 | 400 MHz, DMSO-d$_6$, δ[ppm]: 10.61 (s, 1H), 8.50 (d, J = 2.0 Hz, 1H), 7.94 (d, J = 2.1 Hz, 1H), 7.63-7.57 (m, 4H), 7.36(br s, 2H), 7.09 (br s, 1H), 3.69 (br s, 2H), 1.01 (s, 1H), 0.41 (d, J = 8.2 Hz, 2H), 0.08 (br s, 2H). |
| 57 | 400 MHz, DMSO-d$_6$, δ[ppm]: 10.59 (s, 1H), 8.42 (d, J = 2.1 Hz, 1H), 7.95 (d, J = 2.1 Hz, 1H), 7.80-7.67 (m, 3H), 7.62-7.52 (m, 3H), 7.35 (s, 1H), 3.75 (s, 2H), 3.16 (s, 3H), 1.03 (s, 1H), 0.53-0.30 (m, 2H), 0.13 (d, J = 16.2 Hz, 2H). |
| 60 | 400 MHz, DMSO-d$_6$, δ[ppm]: 10.46 (s, 1H), 8.34 (d, J = 2.1 Hz, 1H), 7.87 (d, J = 2.1 Hz, 1H), 7.65 (t, J = 7.4 Hz, 1H), 7.54 (br s, 1H), 7.36 (br s, 2H), 7.29 (br s, 1H), 7.16 (br s, 2H), 3.62 (br s, 2H), 0.95 (br s, 1H), 0.34 (br s, 2H), 0.07 (s, 2H). |
| 63 | 400 MHz, DMSO-d$_6$, δ[ppm]: 10.55 (br s, 1H), 8.41 (s, 1H), 7.95 (s, 1H), 7.72 (d, J = 24.2 Hz, 1H), 7.61 (s, 1H), 7.39-7.26 (m, 3H), 7.05 (s, 2H), 4.02 (br s, 1H), 1.39 (br s, 1H), 1.24 (s, 3H), 0.53 (d, J = 50.9 Hz, 2H), 0.32 (d, J = 44.6 Hz, 2H). |
| 75 | 400 MHz, DMSO-d$_6$, δ[ppm]: 8.04 (s, 1H), 7.95 (s, 1H), 7.94-7.63 (m, 2H), 7.42-7.35 (m, 3H), 7.12-6.99 (m, 2H), 5.08-4.78 (m, 1H), 1.48-1.43 (m, 1H), 1.34-1.08 (m, 6H). |
| 77 | 400 MHz, DMSO-d$_6$, δ[ppm]: 10.53 (d, J = 25.6 Hz, 1H), 8.41 (s, 1H), 7.95 (s, 1H), 7.77 (d, J = 7.6 Hz, 3H), 7.61 (s, 1H), 7.52 (s, 2H), 7.36 (t, J = 7.2 Hz, 1H), 4.06 (br s, 1H), 3.14 (s, 3H), 1.41 (br s, 1H), 1.25 (d, J = 8.5 Hz, 3H), 0.56 (d, J = 33.0 Hz, 2H), 0.35 (d, J = 43.5 Hz, 2H). |

Other compounds represented by general formula I of this invention can also be prepared according to the methods described above.

FORMULATION EXAMPLES

Example 1: Sample Preparation Method for Emulsifiable Concentrate of Compound 4

TABLE 4

| | Formulation of emulsifiable concentrate of compound 4 | |
|---|---|---|
| Materials | Content 100% consistency (W/W, %) | Remarks |
| Compound 4 | 5 | Active Ingredient |
| Calcium dodecylbenzene sulfonate | 5 | Emulsifier |
| Polyoxyethylene castor oil | 5 | Emulsifier |
| Trimethylbenzene | 85 | Solvent |

Preparation method: the amount of each material in Table 4 was weighed. Trimethylbenzene was added into 250 mL three-necked flask followed by addition of compound 4, calcium dodecylbenzene sulfonate and polyoxyethylene castor oil. The mixture was stirred at 40–50° C. for 1.5 hours and filtered. The emulsion concentrate of 5% compound 4 was obtained.

Example 2: Sample Preparation Method for Wettable Powder of Compound 23

TABLE 5

Formulation of wettable powder of compound 23

| Materials | Content 100% consistency (W/W, %) | Remarks |
|---|---|---|
| compound 23 | 30 | Active Ingredient |
| sodium dodecyl sulfate | 1.5 | Wetting agent |
| sodium lignin sulfonate | 6 | Dispersant |
| kaolin | 62.5 | Carrier |

Preparation method: the amount of each material in Table 5 was weighed. Compound No. 23, sodium dodecyl sulfate, sodium lignosulfonate and kaolin were mixed evenly and pulverized to an average particle size of 10 microns with a jet mill to obtain wettable powder of 300% compound No. 23.

Examples for Bioactivity Tests

Various kinds of pests were tested with the representative compounds of this invention.

Example 1 Indoor Bioactivity Test Against *Mythimna separata*

The leaf dip method was used to assay the insecticidal activity of compounds to strains of *Mythimna sepatata*. Cut above ground part of fresh maize seedlings, about 10 cm. Dip the maize seedlings into the solution prepared with compound of this invention for 10 seconds and dry them in a cool environment. Then cut the dry maize seedlings into 3~5 cm leaf sections and put 3 leaf sections into each petri dish. Put ten of 4th-instar larvae of *Mythimna separatas* into each dish, which was repeated by 3 times. Then the dishes were placed in an illumination incubator and incubated at 25° C. in the dark. Symptoms were investigated on the 1st, 2nd and 3rd day after treatment, and the mortality was calculated.

The insecticidal activity of some compounds of this invention against *Mythimna separate* is ≥90% (mortality of *Mythimna separata*) at 1 ppm on the 3rd day after treatment. The compounds are 4, 8, 22, 23, 26, 37, 38, 39, 41, 44, 47, 52, 57, 60, 62 and 75.

Example 2 Indoor Bioactivity Test Against *Spodoptera exigua* Hiibner

The leaf dip method was used to assay the insecticidal activity of compounds to strains of *Spodoptera exigua* Hiibner. Dip the leaf disc into the solution prepared with compound of this invention for 10 seconds, and dry them in a cool environment. Then place them in Petri dish with 4 discs per dish. Put the filter paper into the Petri dish to moisturize it. Put 10 of *Spodoptera exigua* Hiibners into each dish, which was repeated by 3 times. The dishes were placed in an illumination incubator and incubated at 25° C. with 14 hL: 10 hD illumination. The number of *Spodoptera exigua* Hiibner death was investigated on the 1st, 2nd and 3rd day after treatment, and the mortality was calculated.

The insecticidal activity of some compounds of this invention against *Spodoptera exigua* Hiibner is as follows:

The insecticidal activity of compounds 53, 60, and 75 is ≥90% (mortality of *Spodoptera exigua* Hiibner) at 10 ppm on the 3rd day after treatment.

The insecticidal activity of compounds 4, 23, 37, 41, 46, 47, 57 and 62 is 90% (mortality of *Spodoptera exigua* Hiibner) at 1 ppm on the 3rd day after treatment.

Example 3 Indoor Bioactivity Test Against *Plutella xylostella*

The leaf dip method was used to assay the insecticidal activity of compounds to strains of *Plutella xylostella*. Dip the leaf disc into the solution prepared with compound of this invention for 10 seconds, and dry them in a cool environment. Then place them in Petri dish with 4 discs per dish. Put the filter paper into the Petri dish to moisturize it. Put 10 of *Plutella xylostella* into each dish, which was repeated by 3 times. The dishes were placed in an illumination incubator and incubated at 25° C. with 14 hL: 10 hD illumination. The number of *Plutella xylostella* death was investigated on the 1st, 2nd and 3rd day after treatment, and the mortality was calculated.

The insecticidal activity of some compounds of this invention against *Plutella xylostella* is as follows:

The insecticidal activity of compounds 37, 39, 57, 60, 63 and 75 is ≥90% (mortality of *Plutella xylostella*) at 1 ppm on the 3rd day after treatment.

The insecticidal activity of compounds 4, 8, 23, 26, 41 and 62 is ≥90% (mortality of *Plutella xylostella*) at 0.4 ppm on the 3rd day after treatment.

According to the above method, compound 4 and KC1 were selected and parallelly tested against *Plutella xylostella* to compare their insecticidal activity. The results are shown in Table 6

TABLE 6

The mortality of compound 4 and KC1 against *Plutella xylostella*

| Compound name | Structure | dose | Mortality (%) 1 d | 2 d | 3 d |
|---|---|---|---|---|---|
| Compound 4 | (structure) | 0.04 ppm | 30 | 80 | 100 |

TABLE 6-continued

The mortality of compound 4 and KC1 against *Plutella xylostella*

| Compound name | Structure | dose | Mortality (%) | | |
|---|---|---|---|---|---|
| | | | 1 d | 2 d | 3 d |
| KC1 (broflanilide) | | 0.04 ppm | 0 | 56.67 | 90 |

Table 6 shows that Compound 4 of this invention has better quick-acting effect than KC1 at a low dose. The mortality of *Plutella xylostella* is 30% on the 1st day and 80% on the 2nd day after treatment. It has efficient insecticidal activity.

Example 4 Indoor Bioactivity Test Against *Spodoptera litura*

The leaf dip method was used to assay the insecticidal activity of compounds to strains of *Spodoptera litura*. Dip the leaf disc into the solution prepared with compound of this invention for 10 seconds, and dry them in a cool environment. Then place them in Petri dish with 4 discs per dish. Put the filter paper into the Petri dish to moisturize it. Put 10 of *Spodoptera litura* into each dish, which was repeated by 3 times. The dishes were placed in an illumination incubator and incubated at 25° C. with 14 hL: 10 hD illumination. The number of *Spodoptera litura* death was investigated on the 1st, 2nd and 3rd day after treatment, and the mortality was calculated.

The insecticidal activity of some compounds of this invention against *Spodoptera litura* is as follows:

The insecticidal activity of compounds 4, 52, 53, 57, 75 is ≥90% (mortality of *Spodoptera litura*) at 10 ppm on the 3rd day after treatment.

The insecticidal activity of compounds 23, 37, 41, 47, 60, 62 is ≥90% (mortality of *Spodoptera litura*) at 0.4 ppm on the 3rd day after treatment.

According to the above method, compound 4, 23 and KC1 were selected and parallelly tested against *Spodoptera litura* to compare the insecticidal activity. The results are shown in Table 7.

TABLE 7

The mortality of compound 4, 23 and KC1 on *Spodoptera litura*

| Compound name | Structure | Dose | Mortality (%) | | |
|---|---|---|---|---|---|
| | | | 1 d | 2 d | 3 d |
| Compound 4 | | 1 ppm | 73.33 | 73.33 | 73.33 |
| | | 0.4 ppm | 20.00 | 26.67 | 26.67 |
| Compound 23 | | 1 ppm | 93.33 | 100.00 | 100.00 |
| | | 0.4 ppm | 40.00 | 46.67 | 60.00 |

TABLE 7-continued

The mortality of compound 4, 23 and KC1 on *Spodoptera litura*

| Compound name | Structure | Dose | Mortality (%) 1 d | 2 d | 3 d |
|---|---|---|---|---|---|
| KC1 (broflanilide) | 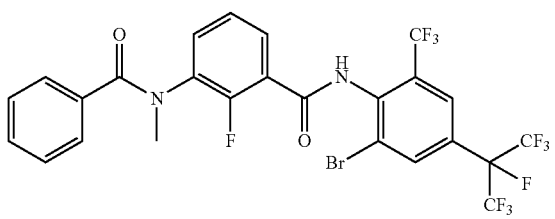 [SMILES: CN(C(=O)c1ccccc1)c1cccc(C(=O)Nc2c(Br)cc(C(F)(C(F)(F)F)C(F)(F)F)cc2C(F)(F)F)c1F] | 1 ppm 0.4 ppm | 26.67 0.00 | 33.33 0.00 | 33.33 0.00 |

The results of Table 7 show that the compounds of this invention have better quick-acting properties and higher insecticidal activity than KC1 at a low dose.

Example 5 Indoor Bioactivity Test Against *Chilo suppressalis*

The leaf dip method was used to assay the insecticidal activity of compounds to strains of *Chilo suppressalis*. The rice was cultivated in a plastic pot with a diameter of 9 cm and a height of 10 cm. When the rice grew about 25 cm, the aerial part of robust and consistent rice seedlings were selectively cut. Their leaves were removed and their stems of about 8 cm were kept for use. Pour the solution prepared with compound of this invention into the Petri dish (about 40 mL) and immerse the rice stems into the solution for 10 seconds. Take rice stems out and dry them in a cool environment. Put a wet cotton ball at the bottom of finger-like glass tube and 5 rice stems in each tube. Put 10 of 3rd-instar larvae of *Chilo suppressa* into each tube, which was repeated by 3 times. Seal the tubes with black cotton cloth and tighten them with rubber band. The tubes were placed in a illumination incubator at 28° C. and incubated in the dark. The number of alive *Chilo suppressalis* and the total number were investigated 3 days after treatment. The mortality was calculated.

The insecticidal activity of some compounds of this invention against *Chilo suppressalis* is as follows:

Compounds 39, 47, 50, 52 and 53 have a good insecticidal effect at 10 ppm on the 3rd day after treatment, and the mortality t is ≥90% (mortality of *Chilo suppressalis*).

Compounds 4, 23, 26, 37, 41, 46 and 62 have a good insecticidal effect at 5 ppm on the 3rd day after treatment, and the mortality is ≥90% (mortality of *Chilo suppressalis*).

According to the above method, Compound 23 and KC2 were selected and parallelly tested against *Chilo suppressalis*. The results are shown in Table 8.

TABLE 8

The mortality of compound 23 and KC2 on *Chilo suppressalis*

| Compound name | Structure | Mortality (%, 3d) 5 ppm | 2 ppm | 1 ppm | 0.4 ppm |
|---|---|---|---|---|---|
| Compound 23 | 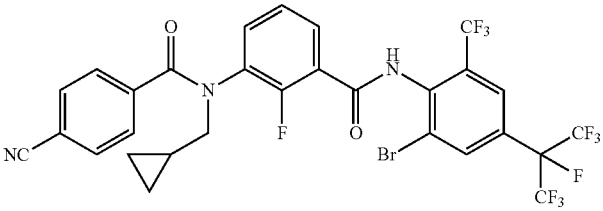 [SMILES: N#Cc1ccc(C(=O)N(CC2CC2)c2cccc(C(=O)Nc3c(Br)cc(C(F)(C(F)(F)F)C(F)(F)F)cc3C(F)(F)F)c2F)cc1] | 100 | 100 | 93.33 | 53.33 |
| KC2 | 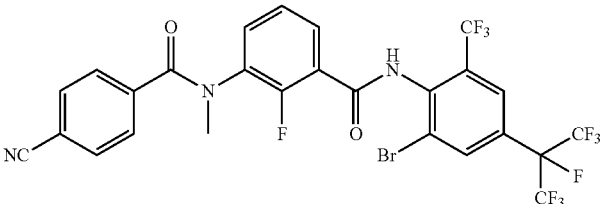 | 93.33 | 86.67 | 53.33 | 0 |

The results of Table 8 show that the compound of this invention has a better insecticidal effect than KC2 at a lower dose.

Example 6 Biological Activity of Compounds on Soybean *Thrips* (in Greenhouse)

Experimental Date: 2018 Aug. 6~2018 Aug. 12

Test system: naturally occurring *thrips* population on soybeans planted in greenhouse. The basic number of active thripses were more than 100 thripses per trifoliate leaf. Under the same conditions, the sensitivity of the *thrips* population to Spinetoram (dose: 50 mg/L) is 96.55% mortality on the 6th day after treatment.

The size of the plot: 10 m$^2$, no repetition.

Test formulation: each compound was made into 5% SL (compound 5%+emulsifier 5%+solvent to make up 100%).

Method: Foliar spray.

① Spraying time: both adult and larva thripses were in the active period. The number of spray: 1 time.

② Standard for water usage: when dose was in mg/kg, the upper leaves were wet and water began to drop therefrom.

③ Survey standard: count three single leaves as one leaf. Three leaves were randomly selected and investigated for the number of adult and larva thripses on them.

④ Survey time and number: surveys were carried out 2 days and 6 days after spray, irrespectively. 2 surveys were conducted.

Results and Analysis: the field activity results of Compound 4 against soybean *thrips* are shown in Table 9.

TABLE 9

Field activity of compound 4 against soybean thrips (June of 2018, Qingpu, Shanghai)

| Compound name | dose ppm | 1 d | | 6 d | |
| --- | --- | --- | --- | --- | --- |
| | | No. of thrips | Mortality % | No. of thrips) | Mortality % |
| Compound 4 | 50 | 6 | 97.73 | 6 | 94.83 |
| | 10 | 20 | 92.42 | 2 | 98.28 |
| Spinetoram | 50 | 16 | 93.94 | 4 | 96.55 |
| Blank control | — | 264 | 0.00 | 116 | 0.00 |

The applicant states that the meta-carboxamido benzamide compounds of this invention, the preparation methods and applications thereof can be illustrated by the above mentioned examples, but this invention is not limited thereto, i.e., which does not mean that the implementation of this invention must rely on the above examples. Those skilled in the art should understand that any improvement to this invention, equivalent replacement of the raw materials for preparing the compounds of this invention, addition of auxiliary ingredients, selection of specific methods, etc., all fall within the scope of protection and disclosure of this invention.

What is claimed is:

1. A kind of meta-carboxamido benzamide compounds of formula I:

Formula I wherein:

Z is selected from the group consisting of H, F, Cl, Br, I, CN, NO$_2$, C$_1$-C$_6$ alkyl, C$_1$-C$_6$ haloalkyl, C$_1$-C$_6$ alkoxyl, C$_1$-C$_6$ haloalkoxyl, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl;

Y$_1$ is selected from the group consisting of F, Cl, Br, I, CN, NO$_2$, C$_1$-C$_6$ alkyl, C$_1$-C$_6$ haloalkyl or C$_1$-C$_6$ haloalkoxyl;

Y$_2$ is C$_1$-C$_6$haloalkyl;

R$_1$ is selected from the group consisting of H, F or OCH$_3$;

R$_2$ is selected from the group consisting of F or CF$_3$;

R$_3$ is selected from the group consisting of H, F, Cl, Br, I, C$_1$-C$_6$ alkyl, C$_1$-C$_6$ haloalkyl, C$_3$-C$_8$ cycloalkyl or C$_3$-C$_8$ halocycloalkyl;

R$_4$ is selected from the group consisting of H or halogen;

W$_1$ and W$_2$ are independently of each other O or S.

2. A kind of meta-carboxamido benzamide compounds according to claim 1, wherein:

R$_1$ is selected from the group consisting of F or OCH$_3$;

R$_2$ is F.

3. A kind of meta-carboxamido benzamide compounds according to claim 1, wherein:

Z is selected from the group consisting of H, F, Cl, Br, I, CN, NO$_2$, trifluoromethyl, pentafluoroethyl, heptafluoroisopropyl, difluoromethoxyl, trifluoromethoxyl, methylsulfinyl, trifluoromethyl sulfinyl, methylsulfonyl or trifluoromethyl sulfonyl;

Y$_1$ is selected from the group consisting of F, Cl, Br, I, CN, NO$_2$, methyl, i-propyl, trifluoromethyl, pentafluoroethyl, heptafluoroisopropyl or trifluoromethoxyl;

Y$_2$ is selected from the group consisting of trifluoromethyl, pentafluoroethyl or heptafluoroisopropyl;

R$_1$ is selected from the group consisting of F or methoxyl;

R$_2$ is F;

R$_3$ is selected from the group consisting of H, F, methyl, ethyl, n-propyl, i-propyl, n-butyl, iso-butyl, t-butyl, n-pentyl, 1-methylbutyl, 2,2-dimethylpropyl, 2-methylbutyl, 1,3-dimethylbutyl, n-hexyl, monofluoromethyl, difluoromethyl, trifluoromethyl, monochloromethyl, dichloromethyl, trichloromethyl, pentafluoroethyl, heptafluoroisopropyl, cyclopropyl, cyclobutyl, cyclopentyl, perfluorocyclopropyl, perfluoro cyclobutyl or perfluorocyclopentyl;

R$_4$ is selected from the group consisting of H, F or Cl;

W$_1$ and W$_2$ are independently of each other O.

4. A kind of meta-carboxamido benzamide compounds according to claim 1, wherein the meta-bisamide derivatives are selected from any one of the compounds below, or a combination of at least two thereof:

N-(2-bromo-4-(perfluoropropan-2-yl)-6-(trifluoromethyl)phenyl)-3-(N-(cyclopropylmethyl)benzamido)-2-fluorobenzamide;

N-(2-bromo-4-(perfluoropropan-2-yl)-6-(trifluoromethyl)phenyl)-3-(N-(1-cyclopropylethyl)benzamido)-2-fluorobenzamide;

N-(2-bromo-4-(perfluoropropan-2-yl)-6-(trifluoromethyl)phenyl)-3-(N-(dicyclopropylmethyl)benzamido)-2-fluorobenzamide;

N-(2-bromo-4-(perfluoropropan-2-yl)-6-(trifluoromethyl)phenyl)-3-(4-cyano-N-(cyclopropylmethyl) benzamido)-2-fluorobenzamide;

N-(2-bromo-4-(1,1,1,3,3,3-hexafluoro-2-methoxypropan-2-yl)-6-(trifluoromethyl)phenyl)-3-(4-cyano-N-(cyclopropylmethyl)benzamido)-2-fluorobenzamide;

N-(2-bromo-4-(perfluoropropan-2-yl)-6-(trifluoromethyl)phenyl)-3-(4-cyano-N-(1-cyclopropylethyl)benzamido)-2-fluorobenzamide;

N-(2-bromo-4-(perfluoropropan-2-yl)-6-(trifluoromethyl)phenyl)-3-(4-cyano-N-(dicyclopropylmethyl)benzamido)-2-fluorobenzamide;

N-(2-bromo-4-(perfluoropropan-2-yl)-6-(trifluoromethyl)phenyl)-3-(N-(cyclopropylmethyl)-4-(trifluoromethyl)benzamido)-2-fluorobenzamide;

N-(2-bromo-4-(1,1,1,3,3,3-hexafluoro-2-methoxypropan-2-yl)-6-(trifluoromethyl)phenyl)-3-(N-(cyclopropylmethyl)-4-(trifluoromethyl)benzamido)-2-fluorobenzamide;

N-(2-bromo-4-(perfluoropropan-2-yl)-6-(trifluoromethyl)phenyl)-3-(N-(1-cyclopropylethyl)-4-(trifluoromethyl)benzamido)-2-fluorobenzamide;

N-(2-bromo-4-(perfluoropropan-2-yl)-6-(trifluoromethyl)phenyl)-3-(4-chloro-N-(cyclopropylmethyl)benzamido)-2-fluorobenzamide;

N-(2-bromo-4-(1,1,1,3,3,3-hexafluoro-2-methoxypropan-2-yl)-6-(trifluoromethyl)phenyl)-3-(4-chloro-N-(cyclopropylmethyl)benzamido)-2-fluorobenzamide;

N-(2-bromo-4-(perfluoropropan-2-yl)-6-(trifluoromethyl)phenyl)-3-(4-chloro-N-(1-cyclopropylethyl)benzamido)-2-fluorobenzamide;

N-(2-bromo-4-(perfluoropropan-2-yl)-6-(trifluoromethyl)phenyl)-3-(4-bromo-N-(cyclopropylmethyl)benzamido)-2-fluorobenzamide;

N-(2-iodo-4-(perfluoropropan-2-yl)-6-(trifluoromethyl)phenyl)-3-(4-bromo-N-(cyclopropylmethyl)benzamido)-2-fluorobenzamide;

N-(2-bromo-4-(1,1,1,3,3,3-hexafluoro-2-methoxypropan-2-yl)-6-(trifluoromethyl)phenyl)-3-(4-bromo-N-(cyclopropylmethyl)benzamido)-2-fluorobenzamide;

N-(2-bromo-4-(perfluoropropan-2-yl)-6-(trifluoromethyl)phenyl)-3-(4-bromo-N-(1-cyclopropylethyl)benzamido)-2-fluorobenzamide;

N-(2-bromo-4-(perfluoropropan-2-yl)-6-(trifluoromethyl)phenyl)-3-(N-(cyclopropylmethyl)-4-iodobenzamido)-2-fluorobenzamide;

N-(2-iodo-4-(perfluoropropan-2-yl)-6-(trifluoromethyl)phenyl)-3-(N-(cyclopropylmethyl)-4-iodobenzamido)-2-fluorobenzamide;

N-(2-bromo-4-(perfluoropropan-2-yl)-6-(trifluoromethyl)phenyl)-3-(N-(cyclopropylmethyl)-4-(methylsulfonyl)benzamido)-2-fluorobenzamide;

N-(2-bromo-4-(perfluoropropan-2-yl)-6-(trifluoromethyl)phenyl)-3-(N-(cyclopropylmethyl)-4-(trifluoromethoxy)benzamido)-2-fluorobenzamide;

N-(2-bromo-4-(perfluoropropan-2-yl)-6-(trifluoromethyl)phenyl)-3-(N-(cyclopropylmethyl)-4-fluorobenzamido)-2-fluorobenzamide;

N-(2-bromo-4-(perfluoropropan-2-yl)-6-(trifluoromethyl)phenyl)-3-(N-(1-cyclopropylethyl)-4-fluorobenzamido)-2-fluorobenzamide;

N-(2-bromo-4-(perfluoropropan-2-yl)-6-(trifluoromethyl)phenyl)-3-(N-(1-(1-chlorocyclopropyl)ethyl)-4-cyanobenzamido)-2-fluorobenzamide; or N-(2-bromo-4-(perfluoropropan-2-yl)-6-(trifluoromethyl)phenyl)-3-(N-(1-cyclopropylethyl)-4-(methylsulfonyl)benzamido)-2-fluorobenzamide.

5. The tautomers, enantiomers, diasteromers or salts of the compounds according to claim 1.

6. An intermediate for preparing compounds according to claim 1, wherein the intermediate is characterized by a structure as shown in formula VIII

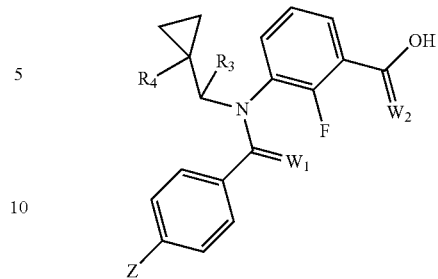

Formula VIII wherein:

Z is selected from the group consisting of H, F, Cl, Br, I, CN, NO$_2$, C$_1$-C$_6$ alkyl, C$_1$-C$_6$ haloalkyl, C$_1$-C$_6$ alkoxyl, C$_1$-C$_6$ haloalkoxyl, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl;

R$_3$ is selected from the group consisting of H, F, Cl, Br, I, C$_1$-C$_6$ alkyl, C$_1$-C$_6$ haloalkyl, C$_3$-C$_8$ cycloalkyl or C$_3$-C$_8$ halocycloalkyl;

R$_4$ is selected from the group consisting of H or halogen,

W$_1$ and W$_2$ are independently of each other O or S.

7. An insecticidal composition, characterized in comprising active ingredient(s) and acceptable carrier in agriculture, wherein the active ingredient(s) are the meta-carboxamido benzamide compounds according to claim 1 or the tautomers, enantiomers, diasteromers or salts thereof.

8. The insecticidal composition according to claim 7, wherein the weight percentage of the active ingredient(s) is 1%-99%.

9. A method for controlling insects, characterized in applying effective concentration of the compounds as defined in claim 1, or the tautomers, enantiomers, diasteromers or salts thereof, to insects or their habitat.

10. The method for controlling insects according to claim 9, wherein the effective concentration is within a range of from 10 g/ha to 1000 g/ha.

11. A method for controlling insects, characterized in applying effective concentration of the composition of claim 7 to insects or their habitat.

12. The method for controlling insects according to claim 9, wherein the effective concentration is within a range of from 25 g/ha to 500 g/ha.

13. A kind of meta-carboxamido benzamide compounds according to claim 3, wherein Z is selected from the group consisting of H, F, Cl, Br, I, CN, NO$_2$, trifluoromethyl, trifluoromethoxyl, methylsulfonyl or trifluoromethyl sulfonyl.

14. A kind of meta-carboxamido benzamide compounds according to claim 3, wherein Y$_1$ is selected from the group consisting of Br or I; Y$_2$ is trifluoromethyl group; R$_1$ is selected from the group consisting of F or methoxyl; R$_2$ is F; R$_3$ is selected from the group consisting of H, methyl or cyclopropyl; R$_4$ is selected from the group consisting of H or Cl.

15. A kind of meta-carboxamido benzamide compounds according to claim 3, wherein Z is CN.

* * * * *